US005891697A

United States Patent [19]

Croteau et al.

[11] Patent Number: 5,891,697

[45] Date of Patent: Apr. 6, 1999

[54] **MONOTERPENE SYNTHASES FROM COMMON SAGE (*SALVIA OFFICINALIS*)**

[75] Inventors: Rodney Bruce Croteau; Mitchell Lynn Wise; Eva Joy Katahira, all of Pullman, Wash.; Thomas Jonathan Savage, Christchurch 5, New Zealand

[73] Assignee: Washington State University Research Foundation

[21] Appl. No.: 937,540

[22] Filed: Sep. 25, 1997

[51] Int. Cl.[6] .............................. C12N 9/10; C12N 15/00; C12N 1/20; C07H 21/04

[52] U.S. Cl. ......................... 435/193; 536/23.2; 536/23.6; 530/350; 435/69.1; 435/252.3; 435/320.1

[58] Field of Search .................................... 435/193, 69.1, 435/252.3, 320.1; 536/23.2, 23.6; 530/350

[56] References Cited

PUBLICATIONS

Croteau, R., and Karp, F., "Biosynthesis of Monoterpenes: Preliminary Characterization of Bornyl Pyrophosphate Synthetase from Sage (*Salvia Officinalis*) and Demonstration that Geranyl Pyrophosphate Is the Preferred Substrate for Cyclization," *Arch. Biochem. Biophys.* 198(2):512–522 (1979).

Croteau, R., and Karp, F., "Biosynthesis of Monoterpenes: Hydrolysis of Bornyl Pyrophosphate, an Essential Step in Camphor Biosynthesis, and Hydrolysis of Geranyl Pyrophosphate, the Acyclic Precursor of Camphor, by Enzymes from Sage (*Salvia Officinalis*)," *Arch Biochem. Biophys.* 198(2):523–532 (1979).

Gambliel, H., and Croteau, R., "Pinene Cyclases I and II," *J. Biol. Chem.* 259(2):740–748 (1984).

Croteau, R.B. et al., "Isotopically Sensitive Branching in the Formation of Cyclic Monoterpenes: Proof That (–)–α–Pinee and (–)–β–Pinene Are Synthesized by the Same Monoterpene Cyclase via Deprotonation of a Common Intermediate," *Biochemistry* 26:5383–5389 (1987).

Croteau, R.B. et al., "Biosynthesis of Monoterpenes," *J. Biol. Chem.* 264(4):2075–2080 (1989).

Wagschal, K. et al., "Isotopically Sensitive Branching as a Tool for Evaluating Multiple Product Formation by Monoterpene Cyclases," *Tetrahedron* 47(31):5933–5944 (1991).

Wagschal, K.C. et al., "Monoterpene Biosynthesis: Isotope Effects Associated with Bicyclic Olefin Formation Catalyzed by Pinene Synthases from Sage (*Salvia officinalis*)," *Arch. Biochem. Biophys.* 308(2):477–487 (1994).

Croteau, R., "The Biosynthesis of Thujane Monoterpenes," In *Recent Developments in Flavor and Fragrance Chemistry* (Hopp, R., and Mori, K., Eds.), VCH Verlagsgesellschaft mbH, Weinheim, Germany, pp. 263–273 (1992).

Croteau, R., "Chapter 2. Monoterpene Biosynthesis. Cyclization of Geranyl Pyrophosphate to (+)–Sabinene," In *Flavor Precursors: Thermal and Enzymatic Conversions* (Teranishi, R., Takeoka, G.R., and Guntert, M., Eds.), American Chemical Society Symposium Series, Fourth Chemical Congress of North America (202nd National Meeting of the American Chemical Society), Washington, DC, No. 490, pp. 8–20, Aug. 25–30, 1991.

ColbyS.M. et al., "4S–Limonene Synthase from the Oil Glands of Spearmint (*Mentha spicata*)," *J. Biol. Chem.* 268(31):23016–23024 (1993).

Pyun, H.–J. et al., "Stereochemistry of the Proton Elimination in the Formation of (+)– and (–)–α–Pinene by Monoterpene Cyclases from Sage (*Salvia officinalis*), " *Arch. Biochem. Biophys.* 308(2):488–496 (1994).

Croteau, R. et al., "Biosynthesis of Monoterpenes: Partial Purification, Characterization, and Mechanism of Action of 1,8–Cineole Synthase," *Arch. Biochem. Biophys.* 309(1):184–192 (1994).

McGeady, P., and Croteau, R., "Isolation and Characterization of an Active–Site Peptide from a Monoterpene Cyclase Labeled with a Mechanism–Based Inhibitor," *Arch Biochem. Biophys.* 317(1):149–155 (1995).

Steele, C.L. et al., "Induced oleoresin biosynthesis in grand fir as a defense against bark beetles," *Proc. Natl. Acad. Sci. USA* 92:4164–4168 (1995).

Yuba, A. et al., "cDNA Cloning, Characterization, and Functional Expression of 4S–(–)–Limonene Synthase from *Perilla frutescens*," *Arch. Biochem. Biophys.* 332(21):280–287 (1996).

Bohlmann, J. et al., "Monoterpene Synthases from Grand Fir (*Abies grandis*)," *J. Biol. Chem.* 272(35):21784–21792 (1997).

*Primary Examiner*—Robert A. Wax
*Assistant Examiner*—Tekchand Saidha
*Attorney, Agent, or Firm*—Christensen O'Connor Johnson & Kindness PLLC

[57] ABSTRACT cDNAs encoding (+)-bornyl diphosphate synthase, 1,8-cineole synthase and (+)-sabinene synthase from common sage (*Salvia officinalis*) have been isolated and sequenced, and the corresponding amino acid sequences has been determined. Accordingly, isolated DNA sequences (SEQ ID No:1; SEQ ID No:3 and SEQ ID No:5) are provided which code for the expression of (+)-bornyl diphosphate synthase (SEQ ID No:2), 1,8-cineole synthase (SEQ ID No:4) and (+)-sabinene synthase SEQ ID No:6), respectively, from sage (*Salvia officinalis*). In other aspects, replicable recombinant cloning vehicles are provided which code for (+)-bornyl diphosphate synthase, 1,8-cineole synthase or (+)-sabinene synthase, or for a base sequence sufficiently complementary to at least a portion of (+)-bornyl diphosphate synthase, 1,8-cineole synthase or (+)-sabinene synthase DNA or RNA to enable hybridization therewith. In yet other aspects, modified host cells are provided that have been transformed, transfected, infected and/or injected with a recombinant cloning vehicle and/or DNA sequence encoding (+)-bornyl diphosphate synthase, 1,8-cineole synthase or (+)-sabinene synthase. Thus, systems and methods are provided for the recombinant expression of the aforementioned recombinant monoterpene synthases that may be used to facilitate their production, isolation and purification in significant amounts. Recombinant (+)-bornyl diphosphate synthase, 1,8-cineole synthase and (+)-sabinene synthase may be used to obtain expression or enhanced expression of (+)-bornyl diphosphate synthase, 1,8-cineole synthase and (+)-sabinene synthase in plants in order to enhance the production of monoterpenoids, or may be otherwise employed for the regulation or expression of (+)-bornyl diphosphate synthase, 1,8-cineole synthase and (+)-sabinene synthase, or the production of their products.

20 Claims, 1 Drawing Sheet

Geranyl Diphosphate

Bornyl Pyrophosphate

Sabinene 1,8-Cineole

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 2025 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: (+)-bornyl diphosphate synthase cDNA from common sage ( i x ) FEATURE:
( A ) NAME/KEY: CDS
( B ) LOCATION: 11..1807

( x i ) SEQUENCE DESCRIPTION: SEQ ID NO:1:

```
GATCACAAAA ATG TCT ATC ATT AGC ATG AAC GTA TCG ATC CTT AGC AAG      49
           Met Ser Ile Ile Ser Met Asn Val Ser Ile Leu Ser Lys
             1               5                  10

CCA CTA AAT TGC CTC CAC AAC TTG GAG AGG AGA CCT TCA AAA GCC TTG      97
Pro Leu Asn Cys Leu His Asn Leu Glu Arg Arg Pro Ser Lys Ala Leu
     15                  20                  25
```

-continued

CTT GTC CCT TGC ACT GCA CCC ACC GCT CGC CTC CGG GCA TCT TGC TCC 145
Leu Val Pro Cys Thr Ala Pro Thr Ala Arg Leu Arg Ala Ser Cys Ser
30                  35                  40                  45

TCA AAA CTA CAA GAA GCT CAT CAA ATC CGA CGA TCT GGA AAC TAC CAA 193
Ser Lys Leu Gln Glu Ala His Gln Ile Arg Arg Ser Gly Asn Tyr Gln
                50                  55                  60

CCT GCC CTT TGG GAT TCC AAT TAC ATT CAG TCT CTC AAT ACT CCA TAT 241
Pro Ala Leu Trp Asp Ser Asn Tyr Ile Gln Ser Leu Asn Thr Pro Tyr
            65                  70                  75

ACG GAG GAG AGG CAC TTG GAT AGA AAA GCA GAG CTG ATT GTG CAA GTG 289
Thr Glu Glu Arg His Leu Asp Arg Lys Ala Glu Leu Ile Val Gln Val
        80                  85                  90

AGG ATA CTG CTA AAG GAA AAA ATG GAG CCT GTT CAA CAA TTG GAG TTG 337
Arg Ile Leu Leu Lys Glu Lys Met Glu Pro Val Gln Gln Leu Glu Leu
    95                  100                 105

ATT CAT GAC TTG AAA TAT TTG GGG CTC TCG GAT TTT TTT CAA GAT GAG 385
Ile His Asp Leu Lys Tyr Leu Gly Leu Ser Asp Phe Phe Gln Asp Glu
110                 115                 120                 125

ATT AAG GAG ATC TTA GGT GTT ATA TAC AAT GAG CAC AAA TGC TTT CAC 433
Ile Lys Glu Ile Leu Gly Val Ile Tyr Asn Glu His Lys Cys Phe His
                130                 135                 140

AAT AAT GAA GTA GAG AAA ATG GAT TTG TAT TTC ACA GCT CTT GGT TTC 481
Asn Asn Glu Val Glu Lys Met Asp Leu Tyr Phe Thr Ala Leu Gly Phe
            145                 150                 155

AGA CTC CTC AGA CAA CAT GGT TTT AAT ATT TCC CAA GAT GTA TTT AAT 529
Arg Leu Leu Arg Gln His Gly Phe Asn Ile Ser Gln Asp Val Phe Asn
        160                 165                 170

TGT TTC AAG AAC GAG AAG GGT ATT GAT TTC AAG GCA AGC CTT GCT CAA 577
Cys Phe Lys Asn Glu Lys Gly Ile Asp Phe Lys Ala Ser Leu Ala Gln
    175                 180                 185

GAT ACG AAG GGA ATG TTA CAA CTG TAT GAA GCG TCT TTC CTT TTG AGA 625
Asp Thr Lys Gly Met Leu Gln Leu Tyr Glu Ala Ser Phe Leu Leu Arg
190                 195                 200                 205

AAA GGT GAA GAT ACA TTG GAG CTT GCA AGA GAA TTT GCC ACA AAA TGT 673
Lys Gly Glu Asp Thr Leu Glu Leu Ala Arg Glu Phe Ala Thr Lys Cys
                210                 215                 220

CTG CAG AAA AAA CTT GAT GAA GGT GGT AAT GAA ATT GAT GAG AAT CTA 721
Leu Gln Lys Lys Leu Asp Glu Gly Gly Asn Glu Ile Asp Glu Asn Leu
            225                 230                 235

TTA TTG TGG ATT CGC CAC TCT TTG GAT CTT CCT CTC CAC TGG AGG ATT 769
Leu Leu Trp Ile Arg His Ser Leu Asp Leu Pro Leu His Trp Arg Ile
        240                 245                 250

CAA AGT GTA GAG GCA AGA TGG TTC ATA GAT GCT TAT GCG AGA AGG CCA 817
Gln Ser Val Glu Ala Arg Trp Phe Ile Asp Ala Tyr Ala Arg Arg Pro
    255                 260                 265

GAC ATG AAT CCA CTT ATT TTC GAG CTT GCC AAA CTC AAC TTC AAT ATT 865
Asp Met Asn Pro Leu Ile Phe Glu Leu Ala Lys Leu Asn Phe Asn Ile
270                 275                 280                 285

ATT CAA GCA ACA CAT CAA CAA GAA CTG AAA GAT CTC TCG AGG TGG TGG 913
Ile Gln Ala Thr His Gln Gln Glu Leu Lys Asp Leu Ser Arg Trp Trp
                290                 295                 300

AGT AGA TTA TGC TTC CCT GAA AAG CTC CCA TTT GTG AGG GAT AGG CTC 961
Ser Arg Leu Cys Phe Pro Glu Lys Leu Pro Phe Val Arg Asp Arg Leu
            305                 310                 315

GTT GAA TCC TTC TTT TGG GCG GTT GGG ATG TTT GAG CCA CAT CAA CAT 1009
Val Glu Ser Phe Phe Trp Ala Val Gly Met Phe Glu Pro His Gln His
        320                 325                 330

GGA TAT CAG AGA AAA ATG GCC GCC ACA ATT ATT GTT TTA GCA ACA GTT 1057
Gly Tyr Gln Arg Lys Met Ala Ala Thr Ile Ile Val Leu Ala Thr Val
    335                 340                 345

-continued

```
ATA GAT GAT ATT TAC GAT GTG TAT GGT ACA CTA GAT GAA CTA GAA CTA    1105
Ile Asp Asp Ile Tyr Asp Val Tyr Gly Thr Leu Asp Glu Leu Glu Leu
350                 355                 360                 365

TTT ACA GAC ACG TTT AAG AGA TGG GAT ACT GAA TCA ATA ACC CGA CTT    1153
Phe Thr Asp Thr Phe Lys Arg Trp Asp Thr Glu Ser Ile Thr Arg Leu
                370                 375                 380

CCT TAT TAC ATG CAA TTA TGT TAT TGG GGT GTC CAC AAC TAT ATT TCC    1201
Pro Tyr Tyr Met Gln Leu Cys Tyr Trp Gly Val His Asn Tyr Ile Ser
            385                 390                 395

GAT GCA GCA TAT GAT ATT CTC AAA GAA CAT GGT TTC TTT TGT CTC CAA    1249
Asp Ala Ala Tyr Asp Ile Leu Lys Glu His Gly Phe Phe Cys Leu Gln
        400                 405                 410

TAT CTC CGG AAA TCG GTG GTA GAT TTG GTT GAA GCA TAT TTT CAC GAG    1297
Tyr Leu Arg Lys Ser Val Val Asp Leu Val Glu Ala Tyr Phe His Glu
    415                 420                 425

GCA AAG TGG TAC CAC AGC GGT TAT ACA CCA AGC CTG GAT GAA TAT CTC    1345
Ala Lys Trp Tyr His Ser Gly Tyr Thr Pro Ser Leu Asp Glu Tyr Leu
430                 435                 440                 445

AAC ATC GCC AAG ATT TCA GTG GCG TCT CCT GCA ATA ATA TCC CCA ACC    1393
Asn Ile Ala Lys Ile Ser Val Ala Ser Pro Ala Ile Ile Ser Pro Thr
                450                 455                 460

TAT TTC ACA TTC GCA AAC GCG TCT CAT GAC ACA GCA GTC ATC GAC AGC    1441
Tyr Phe Thr Phe Ala Asn Ala Ser His Asp Thr Ala Val Ile Asp Ser
            465                 470                 475

TTG TAC CAA TAT CAT GAC ATA CTT TGC CTA GCA GGA ATT ATT TTG AGG    1489
Leu Tyr Gln Tyr His Asp Ile Leu Cys Leu Ala Gly Ile Ile Leu Arg
        480                 485                 490

CTT CCC GAC GAT CTT GGG ACA TCA TAT TTT GAG CTG GCG AGA GGC GAC    1537
Leu Pro Asp Asp Leu Gly Thr Ser Tyr Phe Glu Leu Ala Arg Gly Asp
    495                 500                 505

GTG CCG AAA ACA ATC CAG TGC TAC ATG AAG GAA ACA AAT GCT AGT GAG    1585
Val Pro Lys Thr Ile Gln Cys Tyr Met Lys Glu Thr Asn Ala Ser Glu
510                 515                 520                 525

GAG GAG GCG GTG GAG CAC GTG AAG TTT CTG ATA AGG GAG GCG TGG AAG    1633
Glu Glu Ala Val Glu His Val Lys Phe Leu Ile Arg Glu Ala Trp Lys
                530                 535                 540

GAT ATG AAC ACG GCC ATA GCA GCC GGT TAT CCG TTT CCG GAT GGT ATG    1681
Asp Met Asn Thr Ala Ile Ala Ala Gly Tyr Pro Phe Pro Asp Gly Met
            545                 550                 555

GTG GCG GGC GCA GCT AAT ATT GGG CGC GTG GCG CAG TTT ATT TAT CTC    1729
Val Ala Gly Ala Ala Asn Ile Gly Arg Val Ala Gln Phe Ile Tyr Leu
        560                 565                 570

CAC GGA GAT GGG TTT GGC GTG CAA CAC TCG AAA ACG TAC GAG CAT ATC    1777
His Gly Asp Gly Phe Gly Val Gln His Ser Lys Thr Tyr Glu His Ile
    575                 580                 585

GCC GGC CTA CTG TTC GAG CCT TAT GCA TGA ACAAATGGGA GACTGCTTGA      1827
Ala Gly Leu Leu Phe Glu Pro Tyr Ala  *
590                 595

TATATATTAA TTTGGCACAC CAATAATTGC ATGTTATATA TGTTGGAAAA TAAGTGTCTG  1887

GTTGAGATGT CATGTGGTGT ATTATCTAAA TAATTCAAGG TTGCCTTGTT TATGTAGCCG  1947

GTGGTGCAAC TACCTCCCAT TCAAATCAAT TAAATCTAAA CAGTCGAGTC AAGCTCGAGC  2007

TCGAGGAAAA AAAAAAAA                                                2025
```

( 2 ) INFORMATION FOR SEQ ID NO:2:

( i ) SEQUENCE CHARACTERISTICS:

( A ) LENGTH: 598 amino acids ( B ) TYPE: amino acid ( D ) TOPOLOGY: linear

-continued ( i i ) MOLECULE TYPE: protein ( x i ) SEQUENCE DESCRIPTION: SEQ ID NO:2:

```
Met Ser Ile Ile Ser Met Asn Val Ser Ile Leu Ser Lys Pro Leu Asn
 1               5                  10                  15

Cys Leu His Asn Leu Glu Arg Arg Pro Ser Lys Ala Leu Leu Val Pro
            20                  25                  30

Cys Thr Ala Pro Thr Ala Arg Leu Arg Ala Ser Cys Ser Ser Lys Leu
        35                  40                  45

Gln Glu Ala His Gln Ile Arg Arg Ser Gly Asn Tyr Gln Pro Ala Leu
    50                  55                  60

Trp Asp Ser Asn Tyr Ile Gln Ser Leu Asn Thr Pro Tyr Thr Glu Glu
65                  70                  75                  80

Arg His Leu Asp Arg Lys Ala Glu Leu Ile Val Gln Val Arg Ile Leu
                85                  90                  95

Leu Lys Glu Lys Met Glu Pro Val Gln Gln Leu Glu Leu Ile His Asp
            100                 105                 110

Leu Lys Tyr Leu Gly Leu Ser Asp Phe Phe Gln Asp Glu Ile Lys Glu
        115                 120                 125

Ile Leu Gly Val Ile Tyr Asn Glu His Lys Cys Phe His Asn Asn Glu
    130                 135                 140

Val Glu Lys Met Asp Leu Tyr Phe Thr Ala Leu Gly Phe Arg Leu Leu
145                 150                 155                 160

Arg Gln His Gly Phe Asn Ile Ser Gln Asp Val Phe Asn Cys Phe Lys
                165                 170                 175

Asn Glu Lys Gly Ile Asp Phe Lys Ala Ser Leu Ala Gln Asp Thr Lys
            180                 185                 190

Gly Met Leu Gln Leu Tyr Glu Ala Ser Phe Leu Leu Arg Lys Gly Glu
        195                 200                 205

Asp Thr Leu Glu Leu Ala Arg Glu Phe Ala Thr Lys Cys Leu Gln Lys
    210                 215                 220

Lys Leu Asp Glu Gly Gly Asn Glu Ile Asp Glu Asn Leu Leu Leu Trp
225                 230                 235                 240

Ile Arg His Ser Leu Asp Leu Pro Leu His Trp Arg Ile Gln Ser Val
                245                 250                 255

Glu Ala Arg Trp Phe Ile Asp Ala Tyr Ala Arg Arg Pro Asp Met Asn
            260                 265                 270

Pro Leu Ile Phe Glu Leu Ala Lys Leu Asn Phe Asn Ile Ile Gln Ala
        275                 280                 285

Thr His Gln Gln Glu Leu Lys Asp Leu Ser Arg Trp Trp Ser Arg Leu
    290                 295                 300

Cys Phe Pro Glu Lys Leu Pro Phe Val Arg Asp Arg Leu Val Glu Ser
305                 310                 315                 320

Phe Phe Trp Ala Val Gly Met Phe Glu Pro His Gln His Gly Tyr Gln
                325                 330                 335

Arg Lys Met Ala Ala Thr Ile Ile Val Leu Ala Thr Val Ile Asp Asp
            340                 345                 350

Ile Tyr Asp Val Tyr Gly Thr Leu Asp Glu Leu Glu Leu Phe Thr Asp
        355                 360                 365

Thr Phe Lys Arg Trp Asp Thr Glu Ser Ile Thr Arg Leu Pro Tyr Tyr
    370                 375                 380

Met Gln Leu Cys Tyr Trp Gly Val His Asn Tyr Ile Ser Asp Ala Ala
385                 390                 395                 400

Tyr Asp Ile Leu Lys Glu His Gly Phe Phe Cys Leu Gln Tyr Leu Arg
```

```
                                405                              410                              415
Lys  Ser  Val  Val  Asp  Leu  Val  Glu  Ala  Tyr  Phe  His  Glu  Ala  Lys  Trp
               420                      425                          430

Tyr  His  Ser  Gly  Tyr  Thr  Pro  Ser  Leu  Asp  Glu  Tyr  Leu  Asn  Ile  Ala
               435                      440                          445

Lys  Ile  Ser  Val  Ala  Ser  Pro  Ala  Ile  Ile  Ser  Pro  Thr  Tyr  Phe  Thr
     450                           455                     460

Phe  Ala  Asn  Ala  Ser  His  Asp  Thr  Ala  Val  Ile  Asp  Ser  Leu  Tyr  Gln
465                           470                     475                      480

Tyr  His  Asp  Ile  Leu  Cys  Leu  Ala  Gly  Ile  Ile  Leu  Arg  Leu  Pro  Asp
                    485                      490                          495

Asp  Leu  Gly  Thr  Ser  Tyr  Phe  Glu  Leu  Ala  Arg  Gly  Asp  Val  Pro  Lys
               500                      505                          510

Thr  Ile  Gln  Cys  Tyr  Met  Lys  Glu  Thr  Asn  Ala  Ser  Glu  Glu  Glu  Ala
          515                      520                     525

Val  Glu  His  Val  Lys  Phe  Leu  Ile  Arg  Glu  Ala  Trp  Lys  Asp  Met  Asn
          530                      535                     540

Thr  Ala  Ile  Ala  Ala  Gly  Tyr  Pro  Phe  Pro  Asp  Gly  Met  Val  Ala  Gly
545                           550                     555                      560

Ala  Ala  Asn  Ile  Gly  Arg  Val  Ala  Gln  Phe  Ile  Tyr  Leu  His  Gly  Asp
                    565                      570                          575

Gly  Phe  Gly  Val  Gln  His  Ser  Lys  Thr  Tyr  Glu  His  Ile  Ala  Gly  Leu
               580                      585                          590

Leu  Phe  Glu  Pro  Tyr  Ala
               595
```

( 2 ) INFORMATION FOR SEQ ID NO:3:

( i ) SEQUENCE CHARACTERISTICS:
        ( A ) LENGTH: 1968 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Salvia officinalis ( v i i ) IMMEDIATE SOURCE:
        ( B ) CLONE: 1,8-cineole synthase ( i x ) FEATURE:
        ( A ) NAME/KEY: CDS
        ( B ) LOCATION: 14..1788

( x i ) SEQUENCE DESCRIPTION: SEQ ID NO:3:

```
GGATCACCAC  AAG  ATG  TCG  AGT  CTT  ATA  ATG  CAA  GTT  GTT  ATT  CCT  AAG                49
            Met  Ser  Ser  Leu  Ile  Met  Gln  Val  Val  Ile  Pro  Lys
            1              5                        10

CCA  GCC  AAA  ATT  TTT  CAC  AAT  AAC  TTA  TTC  AGC  GTG  ATT  TCA  AAA  CGA             97
Pro  Ala  Lys  Ile  Phe  His  Asn  Asn  Leu  Phe  Ser  Val  Ile  Ser  Lys  Arg
               15                      20                      25

CAT  CGT  TTC  AGT  ACT  ACA  ATC  ACC  ACT  CGT  GGT  GGC  AGG  TGG  GCA  CAT            145
His  Arg  Phe  Ser  Thr  Thr  Ile  Thr  Thr  Arg  Gly  Gly  Arg  Trp  Ala  His
          30                      35                      40

TGC  TCA  CTA  CAA  ATG  GGT  AAT  GAG  ATC  CAA  ACT  GGA  CGA  CGA  ACT  GGA            193
Cys  Ser  Leu  Gln  Met  Gly  Asn  Glu  Ile  Gln  Thr  Gly  Arg  Arg  Thr  Gly
45                       50                      55                          60
```

-continued

GGC TAC CAG CCT ACC CTT TGG GAT TTC AGC ACC ATT CAA TTG TTC GAC 241
Gly Tyr Gln Pro Thr Leu Trp Asp Phe Ser Thr Ile Gln Leu Phe Asp
65 70 75

TCT GAG TAT AAG GAA GAG AAG CAC TTG ATG AGG GCC GCA GGT ATG ATA 289
Ser Glu Tyr Lys Glu Glu Lys His Leu Met Arg Ala Ala Gly Met Ile
80 85 90

GCC CAA GTG AAT ATG TTG TTG CAG GAA GAA GTA GAT TCG ATT CAA CGG 337
Ala Gln Val Asn Met Leu Leu Gln Glu Glu Val Asp Ser Ile Gln Arg
95 100 105

TTG GAG TTG ATT GAT GAC CTA CGA AGG CTG GGT ATA TCT TGC CAT TTT 385
Leu Glu Leu Ile Asp Asp Leu Arg Arg Leu Gly Ile Ser Cys His Phe
110 115 120

GAC CGC GAG ATC GTT GAA ATA TTA AAC TCA AAA TAT TAT ACC AAC AAT 433
Asp Arg Glu Ile Val Glu Ile Leu Asn Ser Lys Tyr Tyr Thr Asn Asn
125 130 135 140

GAG ATA GAT GAA AGT GAT CTA TAC TCA ACA GCC CTT AGA TTC AAG CTC 481
Glu Ile Asp Glu Ser Asp Leu Tyr Ser Thr Ala Leu Arg Phe Lys Leu
145 150 155

CTA AGA CAA TAC GAT TTT AGC GTC TCT CAA GAG GTA TTT GAT TGT TTC 529
Leu Arg Gln Tyr Asp Phe Ser Val Ser Gln Glu Val Phe Asp Cys Phe
160 165 170

AAG AAT GAC AAG GGT ACT GAT TTC AAG CCA AGC CTA GTC GAT GAT ACT 577
Lys Asn Asp Lys Gly Thr Asp Phe Lys Pro Ser Leu Val Asp Asp Thr
175 180 185

AGA GGA TTG TTA CAA TTG TAC GAA GCT TCG TTT TTA TCA GCA CAA GGC 625
Arg Gly Leu Leu Gln Leu Tyr Glu Ala Ser Phe Leu Ser Ala Gln Gly
190 195 200

GAA GAA ACC CTA CAT CTT GCC AGA GAT TTT GCT ACT AAA TTT CTG CAT 673
Glu Glu Thr Leu His Leu Ala Arg Asp Phe Ala Thr Lys Phe Leu His
205 210 215 220

AAA AGA GTA CTA GTT GAT AAA GAC ATT AAT CTC TTA TCA TCA ATT GAA 721
Lys Arg Val Leu Val Asp Lys Asp Ile Asn Leu Leu Ser Ser Ile Glu
225 230 235

CGT GCG TTG GAG TTG CCT ACT CAT TGG AGG GTT CAA ATG CCC AAC GCA 769
Arg Ala Leu Glu Leu Pro Thr His Trp Arg Val Gln Met Pro Asn Ala
240 245 250

AGA TCC TTC ATT GAT GCT TAT AAG AGG AGA CCC GAC ATG AAT CCG ACT 817
Arg Ser Phe Ile Asp Ala Tyr Lys Arg Arg Pro Asp Met Asn Pro Thr
255 260 265

GTG CTA GAA CTA GCT AAA TTG GAC TTC AAT ATG GTT CAA GCA CAA TTT 865
Val Leu Glu Leu Ala Lys Leu Asp Phe Asn Met Val Gln Ala Gln Phe
270 275 280

CAA CAA GAG CTC AAA GAG GCC TCT AGG TGG TGG AAT AGT ACG GGT CTT 913
Gln Gln Glu Leu Lys Glu Ala Ser Arg Trp Trp Asn Ser Thr Gly Leu
285 290 295 300

GTC CAC GAG CTT CCC TTT GTG AGA GAT AGG ATT GTG GAA TGC TAC TAC 961
Val His Glu Leu Pro Phe Val Arg Asp Arg Ile Val Glu Cys Tyr Tyr
305 310 315

TGG ACG ACA GGA GTG GTT GAG CGT CGT GAA CAT GGA TAC GAG AGG ATA 1009
Trp Thr Thr Gly Val Val Glu Arg Arg Glu His Gly Tyr Glu Arg Ile
320 325 330

ATG CTC ACC AAA ATA AAT GCT CTT GTT ACA ACA ATA GAC GAT GTC TTT 1057
Met Leu Thr Lys Ile Asn Ala Leu Val Thr Thr Ile Asp Asp Val Phe
335 340 345

GAT ATT TAT GGT ACG CTT GAA GAG CTA CAA CTA TTC ACA ACT GCT ATT 1105
Asp Ile Tyr Gly Thr Leu Glu Glu Leu Gln Leu Phe Thr Thr Ala Ile
350 355 360

CAA AGA TGG GAT ATT GAA TCA ATG AAG CAA CTC CCT CCT TAC ATG CAA 1153
Gln Arg Trp Asp Ile Glu Ser Met Lys Gln Leu Pro Pro Tyr Met Gln
365 370 375 380

-continued

ATA TGT TAT CTT GCT CTC TTC AAC TTT GTG AAT GAG ATG GCT TAT GAT 1201
Ile Cys Tyr Leu Ala Leu Phe Asn Phe Val Asn Glu Met Ala Tyr Asp
385 390 395

ACT CTT AGG GAT AAA GGT TTC AAC TCC ACC CCA TAT CTA CGA AAA GCG 1249
Thr Leu Arg Asp Lys Gly Phe Asn Ser Thr Pro Tyr Leu Arg Lys Ala
400 405 410

TGG GTT GAT TTG GTT GAG TCA TAT CTA ATA GAG GCA AAG TGG TAC TAC 1297
Trp Val Asp Leu Val Glu Ser Tyr Leu Ile Glu Ala Lys Trp Tyr Tyr
415 420 425

ATG GGA CAT AAA CCT AGT TTG GAA GAA TAT ATG AAG AAT AGT TGG ATA 1345
Met Gly His Lys Pro Ser Leu Glu Glu Tyr Met Lys Asn Ser Trp Ile
430 435 440

TCA ATC GGA GGC ATC CCC ATT CTA TCT CAT CTA TTT TTC CGG CTA ACA 1393
Ser Ile Gly Gly Ile Pro Ile Leu Ser His Leu Phe Phe Arg Leu Thr
445 450 455 460

GAT TCG ATT GAG GAA GAG GAT GCT GAG AGT ATG CAT AAA TAC CAT GAT 1441
Asp Ser Ile Glu Glu Glu Asp Ala Glu Ser Met His Lys Tyr His Asp
465 470 475

ATT GTT CGT GCA TCG TGT ACT ATT CTA AGG CTT GCT GAT GAT ATG GGA 1489
Ile Val Arg Ala Ser Cys Thr Ile Leu Arg Leu Ala Asp Asp Met Gly
480 485 490

ACA TCG CTG GAT GAG GTG GAG AGA GGC GAC GTG CCC AAA TCA GTT CAG 1537
Thr Ser Leu Asp Glu Val Glu Arg Gly Asp Val Pro Lys Ser Val Gln
495 500 505

TGC TAC ATG AAT GAG AAG AAT GCT TCG GAA GAA GAA GCG CGA GAG CAT 1585
Cys Tyr Met Asn Glu Lys Asn Ala Ser Glu Glu Glu Ala Arg Glu His
510 515 520

GTG CGA TCA CTC ATA GAC CAA ACA TGG AAG ATG ATG AAC AAG GAA ATG 1633
Val Arg Ser Leu Ile Asp Gln Thr Trp Lys Met Met Asn Lys Glu Met
525 530 535 540

ATG ACG TCA TCA TTT TCC AAA TAT TTT GTA CAA GTT TCT GCT AAT CTT 1681
Met Thr Ser Ser Phe Ser Lys Tyr Phe Val Gln Val Ser Ala Asn Leu
545 550 555

GCA AGA ATG GCG CAA TGG ATA TAC CAG CAT GAA TCT GAT GGA TTT GGC 1729
Ala Arg Met Ala Gln Trp Ile Tyr Gln His Glu Ser Asp Gly Phe Gly
560 565 570

ATG CAA CAT TCA TTG GTG AAC AAA ATG CTC AGA GGG TTG TTG TTC GAC 1777
Met Gln His Ser Leu Val Asn Lys Met Leu Arg Gly Leu Leu Phe Asp
575 580 585

CGC TAT GAG TA ACTAATCTTC GCCCGGGTTC CAAATGAATC AATCTGTTGT 1828
Arg Tyr Glu
590

GTTGCTGTTC CACCTGATAT CAATAATAAT TAGACAAATG TTTCTGTACG GGTGGCCCAA 1888

CCGTCAGGCC CATTTCGCTC ATGTTCATAA TAAATAATAA AACTGTTAAT CAATAACAAA 1948

AAAAAAAAAA AAAAAAAAAA 1968

( 2 ) INFORMATION FOR SEQ ID NO:4:

( i ) SEQUENCE CHARACTERISTICS:
( A ) LENGTH: 591 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Ser Ser Leu Ile Met Gln Val Val Ile Pro Lys Pro Ala Lys Ile
1 5 10 15

Phe His Asn Asn Leu Phe Ser Val Ile Ser Lys Arg His Arg Phe Ser
20 25 30

-continued

```
Thr Thr Ile Thr Thr Arg Gly Gly Arg Trp Ala His Cys Ser Leu Gln
         35                  40                  45

Met Gly Asn Glu Ile Gln Thr Gly Arg Arg Thr Gly Gly Tyr Gln Pro
     50                  55                  60

Thr Leu Trp Asp Phe Ser Thr Ile Gln Leu Phe Asp Ser Glu Tyr Lys
 65                  70                  75                  80

Glu Glu Lys His Leu Met Arg Ala Ala Gly Met Ile Ala Gln Val Asn
                 85                  90                  95

Met Leu Leu Gln Glu Glu Val Asp Ser Ile Gln Arg Leu Glu Leu Ile
            100                 105                 110

Asp Asp Leu Arg Arg Leu Gly Ile Ser Cys His Phe Asp Arg Glu Ile
        115                 120                 125

Val Glu Ile Leu Asn Ser Lys Tyr Tyr Thr Asn Asn Glu Ile Asp Glu
    130                 135                 140

Ser Asp Leu Tyr Ser Thr Ala Leu Arg Phe Lys Leu Leu Arg Gln Tyr
145                 150                 155                 160

Asp Phe Ser Val Ser Gln Glu Val Phe Asp Cys Phe Lys Asn Asp Lys
                165                 170                 175

Gly Thr Asp Phe Lys Pro Ser Leu Val Asp Asp Thr Arg Gly Leu Leu
            180                 185                 190

Gln Leu Tyr Glu Ala Ser Phe Leu Ser Ala Gln Gly Glu Glu Thr Leu
        195                 200                 205

His Leu Ala Arg Asp Phe Ala Thr Lys Phe Leu His Lys Arg Val Leu
    210                 215                 220

Val Asp Lys Asp Ile Asn Leu Leu Ser Ser Ile Glu Arg Ala Leu Glu
225                 230                 235                 240

Leu Pro Thr His Trp Arg Val Gln Met Pro Asn Ala Arg Ser Phe Ile
                245                 250                 255

Asp Ala Tyr Lys Arg Arg Pro Asp Met Asn Pro Thr Val Leu Glu Leu
            260                 265                 270

Ala Lys Leu Asp Phe Asn Met Val Gln Ala Gln Phe Gln Gln Glu Leu
        275                 280                 285

Lys Glu Ala Ser Arg Trp Trp Asn Ser Thr Gly Leu Val His Glu Leu
    290                 295                 300

Pro Phe Val Arg Asp Arg Ile Val Glu Cys Tyr Tyr Trp Thr Thr Gly
305                 310                 315                 320

Val Val Glu Arg Arg Glu His Gly Tyr Glu Arg Ile Met Leu Thr Lys
                325                 330                 335

Ile Asn Ala Leu Val Thr Thr Ile Asp Asp Val Phe Asp Ile Tyr Gly
            340                 345                 350

Thr Leu Glu Glu Leu Gln Leu Phe Thr Thr Ala Ile Gln Arg Trp Asp
        355                 360                 365

Ile Glu Ser Met Lys Gln Leu Pro Pro Tyr Met Gln Ile Cys Tyr Leu
    370                 375                 380

Ala Leu Phe Asn Phe Val Asn Glu Met Ala Tyr Asp Thr Leu Arg Asp
385                 390                 395                 400

Lys Gly Phe Asn Ser Thr Pro Tyr Leu Arg Lys Ala Trp Val Asp Leu
                405                 410                 415

Val Glu Ser Tyr Leu Ile Glu Ala Lys Trp Tyr Tyr Met Gly His Lys
            420                 425                 430

Pro Ser Leu Glu Glu Tyr Met Lys Asn Ser Trp Ile Ser Ile Gly Gly
        435                 440                 445

Ile Pro Ile Leu Ser His Leu Phe Phe Arg Leu Thr Asp Ser Ile Glu
```

```
    450                       455                       460

Glu Glu Asp Ala Glu Ser Met His Lys Tyr His Asp Ile Val Arg Ala
465                 470                 475                 480

Ser Cys Thr Ile Leu Arg Leu Ala Asp Asp Met Gly Thr Ser Leu Asp
                485                 490                 495

Glu Val Glu Arg Gly Asp Val Pro Lys Ser Val Gln Cys Tyr Met Asn
            500                 505                 510

Glu Lys Asn Ala Ser Glu Glu Glu Ala Arg Glu His Val Arg Ser Leu
        515                 520                 525

Ile Asp Gln Thr Trp Lys Met Met Asn Lys Glu Met Met Thr Ser Ser
    530                 535                 540

Phe Ser Lys Tyr Phe Val Gln Val Ser Ala Asn Leu Ala Arg Met Ala
545                 550                 555                 560

Gln Trp Ile Tyr Gln His Glu Ser Asp Gly Phe Gly Met Gln His Ser
                565                 570                 575

Leu Val Asn Lys Met Leu Arg Gly Leu Leu Phe Asp Arg Tyr Glu
            580                 585                 590
```

( 2 ) INFORMATION FOR SEQ ID NO:5:

( i ) SEQUENCE CHARACTERISTICS:
( A ) LENGTH: 1911 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Salvia officinalis ( v i i ) IMMEDIATE SOURCE:
( B ) CLONE: (+)-sabinene synthase ( i x ) FEATURE:
( A ) NAME/KEY: CDS
( B ) LOCATION: 25..1792

( x i ) SEQUENCE DESCRIPTION: SEQ ID NO:5:

```
GCAATATTAC AACTAACAAT AAAA ATG TCT TCC ATT AGC ATA AAC ATA GCT        51
                           Met Ser Ser Ile Ser Ile Asn Ile Ala
                             1               5

ATG CCA CTG AAT TCC CTC CAC AAC TTT GAG AGG AAA CCT TCA AAA GCA       99
Met Pro Leu Asn Ser Leu His Asn Phe Glu Arg Lys Pro Ser Lys Ala
 10                  15                  20                  25

TGG TCT ACC TCT TGC ACT GCA CCC GCA GCT CGC CTC CGG GCA TCT TCC      147
Trp Ser Thr Ser Cys Thr Ala Pro Ala Ala Arg Leu Arg Ala Ser Ser
                 30                  35                  40

TCC TTA CAA CAA GAA AAA CCT CAC CAA ATC CGA CGC TCT GGG GAT TAC      195
Ser Leu Gln Gln Glu Lys Pro His Gln Ile Arg Arg Ser Gly Asp Tyr
             45                  50                  55

CAA CCC TCT CTT TGG GAT TTC AAT TAC ATA CAG TCT CTC AAC ACT CCG      243
Gln Pro Ser Leu Trp Asp Phe Asn Tyr Ile Gln Ser Leu Asn Thr Pro
         60                  65                  70

TAT AAG GAG CAG AGA CAC TTT AAT AGG CAA GCA GAG TTG ATT ATG CAA      291
Tyr Lys Glu Gln Arg His Phe Asn Arg Gln Ala Glu Leu Ile Met Gln
     75                  80                  85

GTG AGG ATG TTG CTC AAG GTA AAG ATG GAG GCA ATT CAA CAG TTG GAG      339
Val Arg Met Leu Leu Lys Val Lys Met Glu Ala Ile Gln Gln Leu Glu
 90                  95                 100                 105
```

-continued

```
TTG ATT GAT GAC TTG CAA TAC CTG GGA CTG TCT TAT TTC TTT CAA GAT      387
Leu Ile Asp Asp Leu Gln Tyr Leu Gly Leu Ser Tyr Phe Phe Gln Asp
                110                 115                 120

GAG ATT AAA CAA ATC TTA AGT TCT ATA CAC AAT GAG CCC AGA TAT TTC      435
Glu Ile Lys Gln Ile Leu Ser Ser Ile His Asn Glu Pro Arg Tyr Phe
            125                 130                 135

CAC AAT AAT GAT TTG TAT TTC ACA GCT CTT GGA TTC AGA ATC CTC AGA      483
His Asn Asn Asp Leu Tyr Phe Thr Ala Leu Gly Phe Arg Ile Leu Arg
        140                 145                 150

CAA CAT GGT TTT AAT GTT TCC GAA GAT GTA TTT GAT TGT TTC AAA ATT      531
Gln His Gly Phe Asn Val Ser Glu Asp Val Phe Asp Cys Phe Lys Ile
    155                 160                 165

GAG AAG TGC AGT GAT TTC AAT GCA AAC CTT GCT CAA GAT ACG AAG GGA      579
Glu Lys Cys Ser Asp Phe Asn Ala Asn Leu Ala Gln Asp Thr Lys Gly
170                 175                 180                 185

ATG TTA CAA CTT TAT GAA GCA TCT TTC CTT TTG AGA GAA GGT GAA GAT      627
Met Leu Gln Leu Tyr Glu Ala Ser Phe Leu Leu Arg Glu Gly Glu Asp
                190                 195                 200

ACA TTG GAG CTA GCA AGA CGA TTT TCC ACC AGA TCT CTA CGA GAA AAA      675
Thr Leu Glu Leu Ala Arg Arg Phe Ser Thr Arg Ser Leu Arg Glu Lys
            205                 210                 215

TTT GAT GAA GGT GGT GAT GAA ATT GAT GAA GAT CTA TCA TCG TGG ATT      723
Phe Asp Glu Gly Gly Asp Glu Ile Asp Glu Asp Leu Ser Ser Trp Ile
        220                 225                 230

CGC CAT TCC TTG GAT CTT CCT CTT CAT TGG AGG GTC CAA GGA TTA GAG      771
Arg His Ser Leu Asp Leu Pro Leu His Trp Arg Val Gln Gly Leu Glu
    235                 240                 245

GCA AGA TGG TTC TTA GAT GCT TAT GCG AGG AGG CCG GAC ATG AAT CCA      819
Ala Arg Trp Phe Leu Asp Ala Tyr Ala Arg Arg Pro Asp Met Asn Pro
250                 255                 260                 265

CTT ATT TTC AAA CTC GCC AAA CTC AAC TTC AAT ATT GTT CAG GCA ACA      867
Leu Ile Phe Lys Leu Ala Lys Leu Asn Phe Asn Ile Val Gln Ala Thr
                270                 275                 280

TAT CAA GAA GAA CTG AAA GAT ATC TCA AGG TGG TGG AAT AGT TCG TGC      915
Tyr Gln Glu Glu Leu Lys Asp Ile Ser Arg Trp Trp Asn Ser Ser Cys
            285                 290                 295

CTT GCT GAG AAA CTC CCA TTT GTG AGA GAT AGG ATT GTG GAA TGC TTC      963
Leu Ala Glu Lys Leu Pro Phe Val Arg Asp Arg Ile Val Glu Cys Phe
        300                 305                 310

TTT TGG GCC ATC GCG GCT TTT GAG CCT CAC CAA TAT AGT TAT CAG AGA     1011
Phe Trp Ala Ile Ala Ala Phe Glu Pro His Gln Tyr Ser Tyr Gln Arg
    315                 320                 325

AAA ATG GCC GCC GTT ATT ATT ACT TTC ATA ACA ATT ATC GAT GAT GTT     1059
Lys Met Ala Ala Val Ile Ile Thr Phe Ile Thr Ile Ile Asp Asp Val
330                 335                 340                 345

TAT GAT GTG TAT GGA ACA ATA GAA GAA CTA GAA CTA TTA ACA GAT ATG     1107
Tyr Asp Val Tyr Gly Thr Ile Glu Glu Leu Glu Leu Leu Thr Asp Met
                350                 355                 360

ATT CGC AGA TGG GAT AAT AAA TCA ATA AGC CAA CTT CCA TAT TAT ATG     1155
Ile Arg Arg Trp Asp Asn Lys Ser Ile Ser Gln Leu Pro Tyr Tyr Met
            365                 370                 375

CAA GTG TGC TAT TTG GCA CTA TAC AAC TTC GTT TCT GAG CGG GCT TAC     1203
Gln Val Cys Tyr Leu Ala Leu Tyr Asn Phe Val Ser Glu Arg Ala Tyr
        380                 385                 390

GAT ATT CTA AAA GAT CAA CAT TTC AAC AGC ATC CCA TAT TTA CAG AGA     1251
Asp Ile Leu Lys Asp Gln His Phe Asn Ser Ile Pro Tyr Leu Gln Arg
    395                 400                 405

TCG TGG GTA AGT TTG GTT GAA GGA TAT CTT AAG GAG GCA TAC TGG TAC     1299
Ser Trp Val Ser Leu Val Glu Gly Tyr Leu Lys Glu Ala Tyr Trp Tyr
410                 415                 420                 425
```

-continued

```
TAC AAT GGC TAT AAA CCA AGC TTG GAA GAA TAT CTC AAC AAC GCC AAG      1347
Tyr Asn Gly Tyr Lys Pro Ser Leu Glu Glu Tyr Leu Asn Asn Ala Lys
                430                 435                 440

ATT TCA ATA TCG GCT CCT ACA ATC ATA TCC CAG CTT TAT TTT ACA TTA      1395
Ile Ser Ile Ser Ala Pro Thr Ile Ile Ser Gln Leu Tyr Phe Thr Leu
            445                 450                 455

GCA AAC TCG ATT GAT GAA ACA GCT ATC GAG AGC TTG TAC CAA TAT CAT      1443
Ala Asn Ser Ile Asp Glu Thr Ala Ile Glu Ser Leu Tyr Gln Tyr His
        460                 465                 470

AAC ATA CTT TAC CTA TCA GGA ACC ATA TTA AGG CTT GCT GAC GAT CTT      1491
Asn Ile Leu Tyr Leu Ser Gly Thr Ile Leu Arg Leu Ala Asp Asp Leu
    475                 480                 485

GGG ACA TCA CAA CAT GAG CTG GAG AGA GGA GAC GTA CCG AAA GCA ATC      1539
Gly Thr Ser Gln His Glu Leu Glu Arg Gly Asp Val Pro Lys Ala Ile
490                 495                 500                 505

CAG TGC TAC ATG AAT GAC ACA AAT GCT TCG GAG AGA GAG GCG GTG GAA      1587
Gln Cys Tyr Met Asn Asp Thr Asn Ala Ser Glu Arg Glu Ala Val Glu
                510                 515                 520

CAC GTG AAG TTT CTG ATA AGG GAG GCG TGG AAG GAG ATG AAC ACG GTC      1635
His Val Lys Phe Leu Ile Arg Glu Ala Trp Lys Glu Met Asn Thr Val
            525                 530                 535

ACA ACA GCC AGC GAT TGT CCG TTT ACG GAT GAT TTG GTT GCG GCC GCA      1683
Thr Thr Ala Ser Asp Cys Pro Phe Thr Asp Asp Leu Val Ala Ala Ala
        540                 545                 550

GCT AAT CTT GCA AGG GCG GCT CAG TTT ATA TAT CTC GAC GGG GAT GGG      1731
Ala Asn Leu Ala Arg Ala Ala Gln Phe Ile Tyr Leu Asp Gly Asp Gly
    555                 560                 565

CAT GGC GTG CAA CAC TCA GAA ATA CAT CAA CAG ATG GGA GGC CTG CTA      1779
His Gly Val Gln His Ser Glu Ile His Gln Gln Met Gly Gly Leu Leu
570                 575                 580                 585

TTC CAG CCT TAT  G TCTGAATAAA TCGAAAATCC AACCTACTAT GTATCCCTCG      1832
Phe Gln Pro Tyr
            589

ATAATATATT CTTGGGGTTA ACATGTTTAA TTAAAGTTCT AATTAAAAGA GCTGAATCGA    1892

TCCTCAAAAA AAAAAAAAA                                                 1911
```

( 2 ) INFORMATION FOR SEQ ID NO:6:

( i ) SEQUENCE CHARACTERISTICS:
( A ) LENGTH: 589 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Ser Ser Ile Ser Ile Asn Ile Ala Met Pro Leu Asn Ser Leu His
  1               5                  10                  15

Asn Phe Glu Arg Lys Pro Ser Lys Ala Trp Ser Thr Ser Cys Thr Ala
             20                  25                  30

Pro Ala Ala Arg Leu Arg Ala Ser Ser Ser Leu Gln Gln Glu Lys Pro
         35                  40                  45

His Gln Ile Arg Arg Ser Gly Asp Tyr Gln Pro Ser Leu Trp Asp Phe
     50                  55                  60

Asn Tyr Ile Gln Ser Leu Asn Thr Pro Tyr Lys Glu Gln Arg His Phe
 65                  70                  75                  80

Asn Arg Gln Ala Glu Leu Ile Met Gln Val Arg Met Leu Leu Lys Val
                 85                  90                  95

Lys Met Glu Ala Ile Gln Gln Leu Glu Leu Ile Asp Asp Leu Gln Tyr
```

-continued 100 105 110

Leu Gly Leu Ser Tyr Phe Phe Gln Asp Glu Ile Lys Gln Ile Leu Ser
115 120 125

Ser Ile His Asn Glu Pro Arg Tyr Phe His Asn Asn Asp Leu Tyr Phe
130 135 140

Thr Ala Leu Gly Phe Arg Ile Leu Arg Gln His Gly Phe Asn Val Ser
145 150 155 160

Glu Asp Val Phe Asp Cys Phe Lys Ile Glu Lys Cys Ser Asp Phe Asn
165 170 175

Ala Asn Leu Ala Gln Asp Thr Lys Gly Met Leu Gln Leu Tyr Glu Ala
180 185 190

Ser Phe Leu Leu Arg Glu Gly Glu Asp Thr Leu Glu Leu Ala Arg Arg
195 200 205

Phe Ser Thr Arg Ser Leu Arg Glu Lys Phe Asp Glu Gly Gly Asp Glu
210 215 220

Ile Asp Glu Asp Leu Ser Ser Trp Ile Arg His Ser Leu Asp Leu Pro
225 230 235 240

Leu His Trp Arg Val Gln Gly Leu Glu Ala Arg Trp Phe Leu Asp Ala
245 250 255

Tyr Ala Arg Arg Pro Asp Met Asn Pro Leu Ile Phe Lys Leu Ala Lys
260 265 270

Leu Asn Phe Asn Ile Val Gln Ala Thr Tyr Gln Glu Glu Leu Lys Asp
275 280 285

Ile Ser Arg Trp Trp Asn Ser Ser Cys Leu Ala Glu Lys Leu Pro Phe
290 295 300

Val Arg Asp Arg Ile Val Glu Cys Phe Phe Trp Ala Ile Ala Ala Phe
305 310 315 320

Glu Pro His Gln Tyr Ser Tyr Gln Arg Lys Met Ala Ala Val Ile Ile
325 330 335

Thr Phe Ile Thr Ile Ile Asp Asp Val Tyr Asp Val Tyr Gly Thr Ile
340 345 350

Glu Glu Leu Glu Leu Leu Thr Asp Met Ile Arg Arg Trp Asp Asn Lys
355 360 365

Ser Ile Ser Gln Leu Pro Tyr Tyr Met Gln Val Cys Tyr Leu Ala Leu
370 375 380

Tyr Asn Phe Val Ser Glu Arg Ala Tyr Asp Ile Leu Lys Asp Gln His
385 390 395 400

Phe Asn Ser Ile Pro Tyr Leu Gln Arg Ser Trp Val Ser Leu Val Glu
405 410 415

Gly Tyr Leu Lys Glu Ala Tyr Trp Tyr Tyr Asn Gly Tyr Lys Pro Ser
420 425 430

Leu Glu Glu Tyr Leu Asn Asn Ala Lys Ile Ser Ile Ser Ala Pro Thr
435 440 445

Ile Ile Ser Gln Leu Tyr Phe Thr Leu Ala Asn Ser Ile Asp Glu Thr
450 455 460

Ala Ile Glu Ser Leu Tyr Gln Tyr His Asn Ile Leu Tyr Leu Ser Gly
465 470 475 480

Thr Ile Leu Arg Leu Ala Asp Asp Leu Gly Thr Ser Gln His Glu Leu
485 490 495

Glu Arg Gly Asp Val Pro Lys Ala Ile Gln Cys Tyr Met Asn Asp Thr
500 505 510

Asn Ala Ser Glu Arg Glu Ala Val Glu His Val Lys Phe Leu Ile Arg
515 520 525

-continued

Glu Ala Trp Lys Glu Met Asn Thr Val Thr Thr Ala Ser Asp Cys Pro
530 535 540

Phe Thr Asp Asp Leu Val Ala Ala Ala Ala Asn Leu Ala Arg Ala Ala
545 550 555 560

Gln Phe Ile Tyr Leu Asp Gly Asp Gly His Gly Val Gln His Ser Glu
565 570 575

Ile His Gln Gln Met Gly Gly Leu Leu Phe Gln Pro Tyr
580 585

( 2 ) INFORMATION FOR SEQ ID NO:7:

( i ) SEQUENCE CHARACTERISTICS:
( A ) LENGTH: 2022 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Salvia officinalis ( v i i ) IMMEDIATE SOURCE:
( B ) CLONE: Unknown monoterpene synthase-like sequence ( x i ) SEQUENCE DESCRIPTION: SEQ ID NO:7:

GCAATTCAAG CCAAAAATCA AAGGGAAAAA AATTGTACCT TCTTAAAATG TGTAGCTTTG 60

GAATGCAAAT GGCGTTTCCT AGCAACCCAA TTAAACATCT TCATAACTCA GACATCAAGT 120

CTTCAAAACT AATTTCCAGT AATAGAATTG GTAGCAGTGA TGCTGCTCGC CTCCGCCTGC 180

ATTGCTCCTC GCAGCAACAC GGTGCCGATG AGCTCCAAAC GCACCGACGA TCTGGAAACT 240

ACAGTCCTTC CCGATGGGAT TTCGATTATA TTCAATCACT CCACAGTGAT TATAAGGAAG 300

AAAGACACAG AAGAAGGGCT AGTGAGCTAG TTATGCAAGT GAAGAAGCTA ATAGAGAAAG 360

AAACGGATCC CACTCGACAG TTGGAGCTAA TGGATGACTT GCAGAGGCTG GGCCTGGGTG 420

ATCATTTCCA GGATGAATTC AAGGAAATCT TAATCTCTGT ATATTTGGAC AATAAATATT 480

ACAAGAGTAA TGTGGATAAT ATGAAAAAGG CCGAAAGGGA TTTGTACTCG ACGGCTCTTG 540

CATTCAGACT CCTTAGACAA CATGGTTTTC ATGTTGCTCC AGAGGTGTTG GGGTGTTTCA 600

AGAACGATGA GGGCGACTTC GAACCAAGCC TTGTCCATGA CACCAGAGGA TTGCTGCAAC 660

TGTACGAAGC TTCCTTCTTG CTGACACAAG GCGAAAACAC ACTCGAGTTA GCTAGAGAAT 720

TTGCCTCCAG AATTCTGCAG GAGAAACTAC TGAATGATGA GATTGATGAC ATTAACCTTT 780

CGACATGGAT ACTCAATTCT TTGGACATCC CAATCCATTG GAGGATTGAA AGGGTGAACA 840

CAAGTGTGTG GATAGAAGCA TACAAGAGGC GAGCCGACAT GAATCCAACA GTGCTGGATC 900

TTGCCATACT GGACACCAAT ATTGTACAAG CACAGTATCA GGAGGAACTC AAACAGAACT 960

TACAGTGGTG GAGAAATTCA GGAATTGTGG AGAAGCTTCC CTTCGTGAGG AACAGGCTAG 1020

TGGAGTCCTA CTTTTGGAGC GTTGGGATCG TGCAGCCTCG TCAACATGGA ATTGGAAGAA 1080

TGGCATTGGG CAAATCCATC GCTCTTATAA CAACCATAAA TGATGTTTAT GATGTGTATG 1140

GTACATTAGA AGAACTCGAA CAATTCACAG ACGTCATTCG AAGATGGGAT ATAAGTTCAA 1200

TAGACAAACT CCCTAGCTAT ATGCAACTGT GTTTTCTTGC ACTGCACAAC TTTGTGAACG 1260

ATACGGCCTA TGATGTGCTA AAAGAGCAAG GTTTCAACAT CATCCCATAT CTCCGAAAAT 1320

CGTGGATGGA TTTGGTGGAG GCATATCTGG TGGAGGCCAA GTGGTACCAC AGTGGATACA 1380

| | | | | | | |
|---|---|---|---|---|---|---|
| AACCAAATCT | GGAAGAGTAT | TTGGAGAACT | CATGGATCTC | AGACTCAGGC | CCTGCTGTAC | 1440 |
| TAGCCCAAGC | ATTTTTCGGC | GTAACACATT | CTCTTACAGA | GGAGGCCGTC | CACAGTTTGT | 1500 |
| ACGGACACCA | CGATTTAATT | CGTTCGTCAT | CAATGATTTT | GCGACTTGCT | GATGATCTAG | 1560 |
| GAACCTCTTC | GGAATGGGCC | ATGTGAAACG | GGACAGTCCA | ATTTGGAAAG | TGGGCCATGT | 1620 |
| GAAACGAGAC | GGAGGGAGTA | ATACATCAAC | AAATCAACAC | TTGCTTCTTC | CACCCTGCAA | 1680 |
| CACTCTAGCT | ACGTACCTAT | GTATATATTA | TATATGCATA | TGCATTGCTT | GCACACATTA | 1740 |
| ATCAAGGAAT | AATCAATGCA | TCACCATATA | TATCTACTTC | TATTTTATAT | GTTCTACTTC | 1800 |
| TAACCTTTCG | TTTAGTATCA | TTAAATTTTC | TTTTATTTTA | TATATTATGT | TTTGAATTGA | 1860 |
| AGCTGTTTTT | ACTGTCTTTA | ATTCACTATA | AACAAATATT | GCGTATATTT | TCGAGAATGG | 1920 |
| AATTAATAAC | ATGATTTTTG | AGAAAAAAAA | TGAAATTATG | TAGGAATTAA | AGATAAAATT | 1980 |
| TGAAAAAAAA | AAAAAAAAAA | CTCGAGGGGG | GCCCGTACCC | AA | | 2022 |

( 2 ) INFORMATION FOR SEQ ID NO:8:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: Oligonucleotide PCR primer 1F where "N"is in ( i i i ) HYPOTHETICAL: NO ( i v ) ANTI-SENSE: NO ( x i ) SEQUENCE DESCRIPTION: SEQ ID NO:8:

AARAAYGARR ARGGNGANTA YAARGA 26

( 2 ) INFORMATION FOR SEQ ID NO:9:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: Oligonucleotide PCR primer 2F where "N"is inosine ( i i i ) HYPOTHETICAL: NO ( i v ) ANTI-SENSE: NO ( x i ) SEQUENCE DESCRIPTION: SEQ ID NO:9:

YTNCARYTNT AYGARGC 17

( 2 ) INFORMATION FOR SEQ ID NO:10:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: Oligonucleotide PCR primer 3R where "N"is inosine 3R"

( i i i ) HYPOTHETICAL: NO ( i v ) ANTI-SENSE: NO ( x i ) SEQUENCE DESCRIPTION: SEQ ID NO:10:

CTRGTYRANG GNMTRATRTA CGTY 24

( 2 ) INFORMATION FOR SEQ ID NO:11:

( i ) SEQUENCE CHARACTERISTICS:
( A ) LENGTH: 659 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Salvia officinalis ( v i i ) IMMEDIATE SOURCE:
( B ) CLONE: hi affinity cDNA probe used for screening sage cDNA library ( x i ) SEQUENCE DESCRIPTION: SEQ ID NO:11:

TTGCATGCCT GCAGGTCGAC TCTAGAGGAT CTACTAGTCA TATGGATTGG TCTAGATTGC 60

ATGTAATCGG GGAGGTTGTC GATTGAACTC ATATCCCATC TTCGAATGAC GTCTGTGAAT 120

TGTTCCAGTT CTTCCAAAGT ACCATACACA TCGTAAACAT CATCTATCGT GGTTATAAGA 180

GCATTCACTT TGCCCACCGT TATCCTTGCA TTTGCATGCT GACGAGGCTG CACGATCCCA 240

GTAGTCCAGA AGTAGCATTC CACAAGTCGG TCCCTCGCGA AGGGGAGCTT CTCCACGATG 300

CACGTACTTC TCCACCACTG TAAGTCCTGT TTGAGTTCCT CTTGATATTG TGCTTGTACA 360

ATATTCGAGT CCAGTATGGC AAGCTCCAAC ACGATGGATT CATGTCGGAT CTCCTCTTAT 420

AGGCATCGAT CCACGTGCTT GCATTTCCTC TTCCAATCCT CCAATGGATT GGGATGTCCA 480

AAGCATAGCG TATCGACAAT AAAAGGTAAA GGTCTTCGTT ACTTTCCTCC TTCAGTTTGT 540

CCTCAAGGAT TTTGGCGGCG AACTCCCTGC CTAAATCCAG CGTCTTCTCA CCTTCCATCG 600

TCAAAAACGA AGCTTCGTAC AATTGCAGCA TAATCGGATC CCCGGTACCG AGCTCGAAN 659

( 2 ) INFORMATION FOR SEQ ID NO:12:

( i ) SEQUENCE CHARACTERISTICS:
( A ) LENGTH: 584 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Salvia officinalis ( v i i ) IMMEDIATE SOURCE:
( B ) CLONE: Low affinity cDNA probe ( x i ) SEQUENCE DESCRIPTION: SEQ ID NO:12:

GGTCTAGACT TCATGTAGTC GGGGAGGTTG TCTATTGAAC TTATATCCCA TCTTCGAATG 60

ACGTCTGTGA ACTGTTCGAG TTCTTCTAAT GTACCATACA CATCATAAAC ATCATTTATG 120

GTTGTTATAA GAGCGATGGA TTTGCCCAAT GCCATTCTTC CAATTCCATG TTGACGAGGC 180

-continued

| | | | | | | |
|---|---|---|---|---|---|---|
| TGCACGATCC | CAACGCTCCA | AAAGTAGGAC | TCCACTAGCC | TGTTCCTCAC | GAAGGGAAGC | 240 |
| TTCTCCACAA | TTCCTGAATT | TCTCCACCAC | TGTAAGTTCT | GTTTGAGTTC | CTCCTGATAC | 300 |
| TGTGCTTGTA | CAATATTGGT | GTCCAGTATG | GCAAGATCCA | GCACTGTTGG | ATTCATGTCG | 360 |
| GCTCGCCTCT | TGTATGCTTC | TATCCACACA | CTTGTGTTCA | CCCTTTCAAT | CCTCCAATGG | 420 |
| ATTGGGATGT | CCAAAGAATT | GAGTATCCAT | GTCGAAAGGT | TAATGTCATC | AATCTCATCA | 480 |
| TTCAGTAGTT | TCTCCTGCAG | AATTCTGGAG | GCAAATTCTC | TAGCTAACTC | GAGTGTGTTT | 540 |
| TCGCCTTGTG | TCAGCAAGAA | GGAAGCCTCG | TACAACTGCA | GCAT | | 584 |

( 2 ) INFORMATION FOR SEQ ID NO:13:

( i ) SEQUENCE CHARACTERISTICS:
( A ) LENGTH: 6 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( D ) OTHER INFORMATION: Universally conserved sequence found in all prenyltransf ( x i ) SEQUENCE DESCRIPTION: SEQ ID NO:13:

Xaa Asp Asp Xaa Xaa Asp
5

( 2 ) INFORMATION FOR SEQ ID NO:14:

( i ) SEQUENCE CHARACTERISTICS:
( A ) LENGTH: 5 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( D ) OTHER INFORMATION: Conserved amino acid found in prenyl transferases. Xaa ( x i ) SEQUENCE DESCRIPTION: SEQ ID NO:14:

Cys Tyr Met Xaa Xaa
1 5

( 2 ) INFORMATION FOR SEQ ID NO:15:

( i ) SEQUENCE CHARACTERISTICS:
( A ) LENGTH: 10 amino acids
( B ) TYPE: amino acid
( C ) STRANDEDNESS: Not Relevant
( D ) TOPOLOGY: Not Relevant ( i i ) MOLECULE TYPE: peptide ( i i i ) HYPOTHETICAL: NO ( i v ) ANTI-SENSE: NO -continued ( v ) FRAGMENT TYPE: internal ( i x ) FEATURE:
( D ) OTHER INFORMATION: Active site peptide.

( x i ) SEQUENCE DESCRIPTION: SEQ ID NO:15:

```
Leu Gln Leu Tyr Glu Ala Ser Phe Leu Leu
1               5                   10
```

MONOTERPENE SYNTHASES FROM COMMON SAGE (*SALVIA OFFICINALIS*)

This invention was supported in part by grant numbers GM-31354 and DE-F603-9620212. The government has certain rights in the invention.

FIELD OF THE INVENTION

The present invention relates to nucleic acid sequences which code for monoterpene synthases (cyclases) from common sage (*Salvia officinalis*), and to vectors containing the sequences, host cells containing the sequences and methods of producing recombinant monoterpene synthases and their mutants.

BACKGROUND OF THE INVENTION

The cyclization of the universal precursor geranyl diphosphate (GPP) to form monocyclic and bicyclic monoterpenes is catalyzed by a group of enzymes termed monoterpene synthases (or cyclases). The biochemical transformation of GPP to cyclic products has been investigated using enzymes from a variety of plants, including both angiosperms (Croteau, R., *Chem. Rev.* 87:929–954, 1987) and gymnosperms (Lewinsohn et at., *Arch. Biochem. Biophys.* 293:167–173, 1992; Savage et al., i J. Biol. Chem. 269:4012–4020, 1994; Savage et al., *Arch. Biochem. Biophys.* 320:257–265, 1995). A mechanistic paradigm for these transformations is well established (Croteau, R., *Chem. Rev.* 87:929–954, 1987; Wise, M. L., and Croteau, R., in *Comprehensive Natural Products Chemistry: Isoprenoids* (Cane, D. E., ed) Vol. 2 (in press), Elsevier Science, Oxford, 1998). In summary, geranyl diphosphate is initially ionized and isomerized to form either 3R- or 3S-linalyl diphosphate, depending on the particular enzyme, which is converted to the α-terpinyl cation as a central intermediate. Further transformations of this reactive intermediate may be effected by additional intramolecular electrophilic additions, hydride shifts or other rearrangements before termination of the sequence by deprotonation of the final cation or capture by an external nucleophile, such as a hydroxyl ion or the diphosphate group. Although the fate of the substrate has been well characterized in numerous monoterpene cyclization reactions, the molecular mechanisms by which the enzymes effect these transformations is still poorly understood.

Culinary sage (*Salvia officinalis*) produces a number of monoterpenes, including (+)- and (−)-α-pinene, (+)- and (−)-β-pinene, (+)- and (−)-camphene, (+)-sabinene, (+)- and (−)-limonene, myrcene, 1,8-cineole, and (+)-bornyl diphosphate (Croteau, R., *Chem. Rev.* 87:929–954, 1987). Because sage produces this broad range of acyclic, monocyclic and bicyclic monoterpenes, including several olefin isomers, a cyclic ether and a diphosphate ester, this plant has provided an ideal system for the study of a variety of biosynthetic enzymes, all of which utilize the same substrate but produce different products by variations on a single reaction mechanism (Croteau, R., *Chem. Rev.* 87:929–954, 1987; Wise, M. L., and Croteau, R., in *Comprehensive Natural Products Chemistry: Isoprenoids* (Cane, D. E., ed) Vol. 2 (in press), Elsevier Science, Oxford, 1998). These monoterpene synthases include (+)-bornyl diphosphate synthase (the enzyme producing the precursor of (+)-camphor) (Croteau, R., and Karp, F., *Arch. Biochem. Biophys.* 198:512–522, 1979; Croteau, R., and Karp, F., *Arch. Biochem. Biophys.* 198:523–532, 1979), 1,8-cineole synthase (Croteau et al, *Arch. Biochem. Biophys.* 309:184–192, 1994), (+)-sabinene synthase (the enzyme producing the precursor of (−)-3-isothujone) (Croteau, R., in *Recent Developments in Flavor and Fragrance Chemistry* (Hopp, R., and Mori, K., eds), pp. 263–273, VCH, Weinheim, Germany, 1992; Croteau, R., in *Flavor Precursors: Thermal and Enzymatic Conversions* (Teranishi, R., Takeoka, G. R., and Guntert, M., eds), American Chemical Society Symposium Series, No. 490, pp. 8–20, Washington, DC, 1992), and several pinene synthases (Gambliel, H., and Croteau, R., *J. Biol. Chem.* 257:2335–2342, 1982; Gambliel, H., and Croteau, R., *J. Biol. Chem.* 259:740–748, 1984; Wagschal et al., *Arch. Biochem. Biophys.* 308:477–487, 1994; Pyun et al., *Arch. Biochem. Biophys.* 308:488–496, 1994).

As is typical of monoterpene cyclases, many of these enzymes from sage generate multiple products from geranyl diphosphate (Wise, M. L., and Croteau, R., in *Comprehensive Natural Products Chemistry: Isoprenoids* (Cane, D. E., ed) Vol. 2 (in press), Elsevier Science, Oxford, 1998; Wagschal et al., *Tetrahedron* 47:5933–5944, 1991). For example, investigations with the partially purified native enzymes have suggested that a single enzyme, termed (+)-pinene synthase (cyclase I), is responsible for the synthesis of both (+)-α-pinene and (+)-camphene, with lesser amounts of (+)-limonene and myrcene, whereas a second enzyme, (−)-pinene synthase (cyclase II), has been shown to produce (−)-α-pinene, (−)-β-pinene and (−)-camphene, with minor amounts of (−)-limonene, terpinolene and myrcene (Gambliel, H., and Croteau, R., *J. Biol. Chem.* 257:2335–2342, 1982; Gambliel, H., and Croteau, R., *J. Biol. Chem.* 259:740–748, 1984).

More recently, a third synthase from sage, termed cyclase III, has been described which produces a mixture of (+)-α-pinene and (+)-β-pinene, along with minor amounts of myrcene (Wagschal et al., *Arch. Biochem. Biophys.* 308:477–487, 1994; Pyun et al., *Arch. Biochem. Biophys.* 308:488–496, 1994). Evidence that these reactions are catalyzed by individual, multifunctional enzymes is provided by co-purification and differential inhibition studies (Gambliel, H., and Croteau, R., *J. Biol. Chem.* 259:740–748, 1984), as well as by isotopically sensitive branching experiments (Wagschal et al., *Arch. Biochem. Biophys.* 308:477–487, 1994; Wagschal et al., *Tetrahedron* 47:5933–5944, 1991; Croteau et al., *Biochemistry* 26:5383–5389, 1987). In spite of considerable effort, the (+)-pinene synthase has never been chromatographically separated from the aforementioned (+)-bornyl diphosphate synthase, suggesting that (+)-bornyl diphosphate synthase and (+)-pinene synthase might, in fact, be a single, multifunctional enzyme (McGeady, P., and Croteau, R., *Arch. Biochem. Biophys.* 317:149–155, 1995). Similarly, the (−)-pinene synthase has never been fully resolved from 1,8-cineole synthase, although, in this case, stereochemical considerations indicate that the two are distinct enzyme species (Croteau et al., *Arch. Biochem. Biophys.* 309:184–192, 1994; Croteau et al., *J. Biol. Chem.* 264:2075–2080, 1989).

The unusual ability of the monoterpene synthases to synthesize multiple products from a single substrate requires the nomenclature of these enzymes to be based on the identity of the principal product synthesized by each enzyme. Thus, starting from the common precursor geranyl diphosphate, (+)-bornyl diphosphate synthase characteristically produces a mixture of monoterpenes of which at least 60% is (+)-bornyl diphosphate; 1,8-cineole synthase characteristically produces a mixture of monoterpenes of which at least 60% is 1,8-cineole and (+)-sabinene synthase characteristically produces a mixture of monoterpenes of which at least 60% is (+)-sabinene.

SUMMARY OF THE INVENTION

In accordance with the foregoing, cDNAs encoding (+)-bornyl diphosphate synthase, 1,8-cineole synthase and (+)-sabinene synthase from common sage (*Salvia officinalis*) have been isolated and sequenced, and the corresponding amino acid sequences have been deduced. Accordingly, the present invention relates to isolated DNA sequences which code for the expression of (+)-bornyl diphosphate synthase, such as the sequence designated SEQ ID No:1 which encodes (+)-bornyl diphosphate synthase from common sage (*Salvia officinalis*), for the expression of 1,8-cineole synthase, such as the sequence designated SEQ ID No:3, which encodes 1,8-cineole synthase from common sage (*Salvia officinalis*), and for the expression of (+)-sabinene synthase, such as the sequence designated SEQ ID No:5, which encodes the (+)-sabinene synthase from common sage (*Salvia officinalis*). In other aspects, the present invention is directed to replicable recombinant cloning vehicles comprising a nucleic acid sequence, e.g., a DNA sequence which codes for a (+)-bornyl diphosphate synthase, 1,8-cineole synthase or (+)-sabinene synthase, or for a base sequence sufficiently complementary to at least a portion of DNA or RNA encoding (+)-bornyl diphosphate synthase, 1,8-cineole synthase or (+)-sabinene synthase to enable hybridization therewith (e.g., antisense RNA or fragments of DNA complementary to a portion of DNA or RNA molecules encoding (+)-bornyl diphosphate synthase, 1,8-cineole synthase or (+)-sabinene synthase which are useful as polymerase chain reaction primers or as probes for any of the foregoing synthases or related genes). In yet other aspects of the invention, modified host cells are provided that have been transformed, transfected, infected and/or injected with a recombinant cloning vehicle and/or DNA sequence of the invention. Thus, the present invention provides for the recombinant expression of (+)-bornyl diphosphate synthase, 1,8-cineole synthase and (+)-sabinene synthase, and the inventive concepts may be used to facilitate the production, isolation and purification of significant quantities of recombinant (+)-bornyl diphosphate synthase, 1,8-cineole synthase and (+)-sabinene synthase (or of their primary enzyme products) for subsequent use, to obtain expression or enhanced expression of (+)-bornyl diphosphate synthase, 1,8cineole synthase and (+)-sabinene synthase in plants, microorganisms or animals, or may be otherwise employed in an environment where the regulation or expression of (+)-bornyl diphosphate synthase, 1,8-cineole synthase and (+)-sabinene synthase is desired for the production of these synthases, or their enzyme products, or derivatives thereof.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
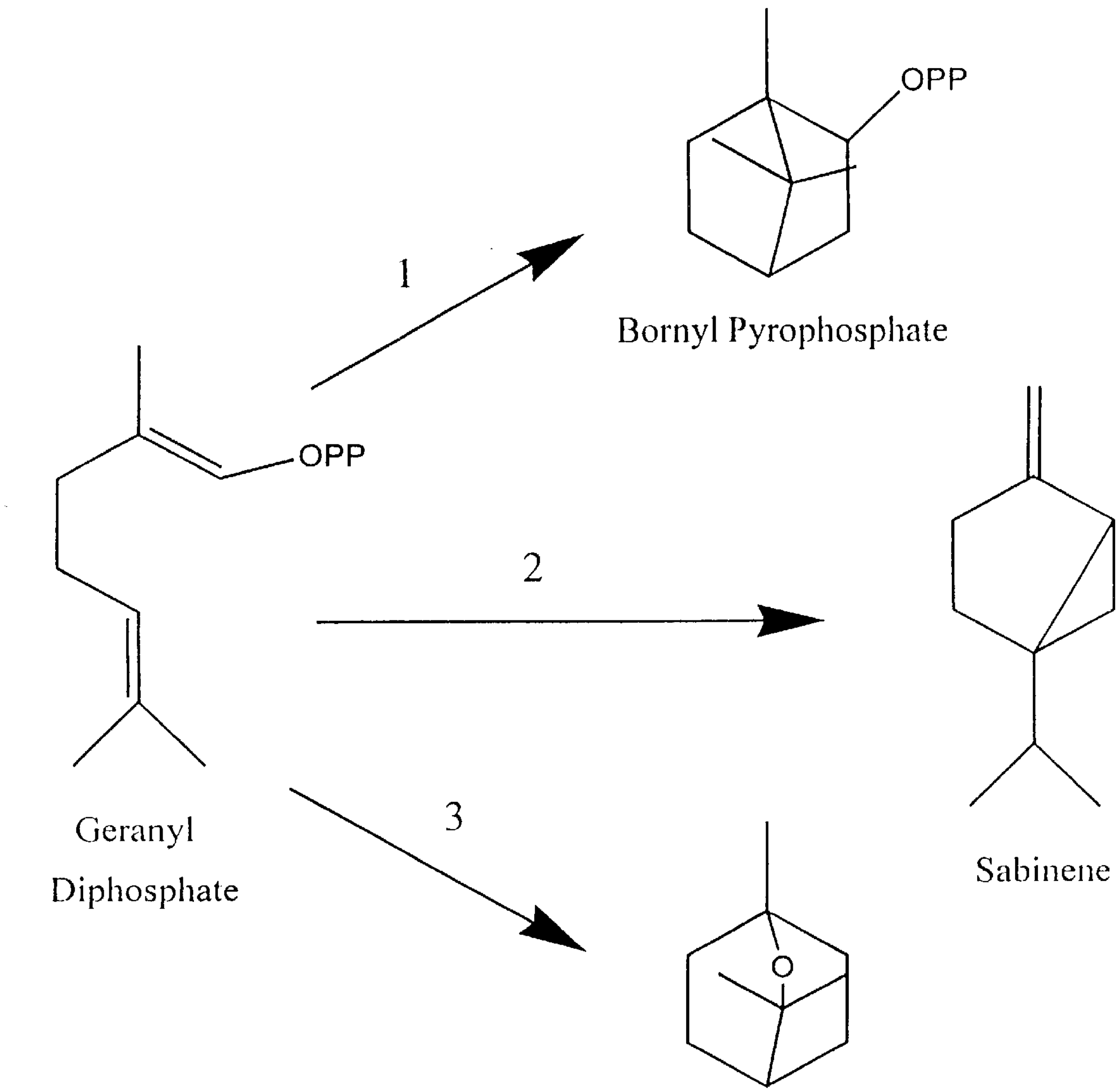
FIGURE 1 shows the terpenoid biosynthetic reactions catalyzed by (+)-bornyl diphosphate synthase (1), (+)-sabinene synthase (2) and 1,8-cineole synthase (3).

As used herein, the terms "amino acid" and "amino acids" refer to all naturally occurring L-α-amino acids or their residues. The amino acids are identified by either the single-letter or three-letter designations:

| | | | | | |
|---|---|---|---|---|---|
| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

The term "percent identity" means the percentage of amino acids or nucleotides that occupy the same relative position when two amino acid sequences, or two nucleic acid sequences are aligned side by side.

The term "percent similarity" is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences have been made empirically by iterative comparison of all possible alignments. (Henikoff, S. and Henikoff, J. G., *Proc. Nat'l Acad Sci USA* 89:10915–10919,1992).

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "(+)-bornyl diphosphate synthase" is used herein to mean an enzyme capable of generating multiple monoterpenes from geranyl diphosphate. The principal and characteristic monoterpene synthesized by (+)-bornyl diphosphate synthase is bornyl pyrophosphate, which comprises at least 60% of the monoterpene mixture synthesized by (+)-bornyl diphosphate synthase from geranyl diphosphate.

The term "(+)-sabinene synthase" is used herein to mean an enzyme capable of generating multiple monoterpenes from geranyl diphosphate. The principal and characteristic monoterpene synthesized by (+)-sabinene synthase is sabinene, which comprises at least 60% of the monoterpene mixture synthesized by (+)-sabinene synthase from geranyl diphosphate.

The term "1,8-cineole synthase" is used herein to mean an enzyme capable of generating multiple monoterpenes from geranyl diphosphate. The principal and characteristic monoterpene synthesized by 1,8-cineole synthase is 1,8 cineole, which comprises at least 60% of the monoterpene mixture synthesized by 1,8-cineole synthase from geranyl diphosphate.

The terms "alteration", "amino acid sequence alteration", "variant" and "amino acid sequence variant" refer to (+)-bornyl diphosphate synthase, (+)-sabinene synthase and 1,8-cineole synthase molecules with some differences in their amino acid sequences as compared to the corresponding, native, i.e., naturally-occurring, synthases. Ordinarily, the variants will possess at least about 70% homology with the corresponding native synthases, and preferably, they will be at least about 80% homologous with the corresponding, native synthases. The amino acid sequence variants of (+)-bornyl diphosphate synthase, (+)-sabinene synthase and 1,8-cineole synthase falling within this invention possess substitutions, deletions, and/or insertions at certain positions. Sequence variants of (+)-bornyl diphosphate synthase, (+)-sabinene synthase and 1,8-cineole synthase may be used to attain desired enhanced or reduced enzymatic activity, modified regiochemistry or stereochemistry, or altered substrate utilization or product distribution.

Substitutional (+)-bornyl diphosphate synthase, (+)-sabinene synthase and 1,8-cineole synthase variants are those that have at least one amino acid residue in the native synthase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the (+)-bomyl diphosphate synthase, (+)-sabinene synthase and 1,8-cineole synthase molecules may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the (+)-bornyl diphosphate synthase, (+)-sabinene synthase and 1,8-cineole synthase molecules would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional (+)-bornyl diphosphate synthase, (+)-sabinene synthase and 1,8-cineole synthase variants are those with one or more amino acids inserted immediately adjacent to an amino acid at a particular position in the native synthase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native (+)-bornyl diphosphate synthase, (+)-sabinene synthase and 1,8-cineole synthase molecules have been removed. Ordinarily, deletional variants will have one or two amino acids deleted in a particular region of the (+)-bornyl diphosphate synthase, (+)-sabinene synthase or 1,8-cineole synthase molecule.

The terms "biological activity", "biologically active", "activity" and "active" refer to the ability of (+)-bornyl diphosphate synthase, (+)-sabinene synthase and 1,8-cineole synthase molecules to convert geranyl diphosphate to a group of monoterpenes, of which bornyl pyrophosphate is the principal and characteristic monoterpene synthesized by (+)-bornyl diphosphate synthase, sabinene is the principal and characteristic monoterpene synthesized by (+)-sabinene synthase and 1,8-cineole is the principal and characteristic monoterpene synthesized by 1,8-cineole synthase. The monoterpenes produced by (+)-bornyl diphosphate synthasc, (+)-sabinene synthase and 1,8-cineole synthase are as measured in an enzyme activity assay, such as the assay described in Example 3. Amino acid sequence variants of (+)-bornyl diphosphate synthase, (+)-sabinene synthase and 1,8-cineole synthase may have desirable altered biological activity including, for example, altered reaction kinetics, substrate utilization product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

The following abbreviations are used herein: bp(s), base pair(s); DEAE, O-diethylaminoethyl; DTT, dithiothreitol; EDTA, ethylenediaminetetraacetic acid; GC, gas chromatography; IPTG, isopropyl-β-D-thiogalactopyranoside; LB, Luria-Bertani; Mopso, 3-(N-morpholino)-2-hydroxypropane-sulfonic acid; MS, mass spectrum/spectrometry; nt(s), nucleotide(s); ORF, open reading frame; PCR, polymerase chain reaction; PVDF, polyvinylidenedifluoride; SDS, sodium dodecyl sulfate; SBS, sage bornyl diphosphate synthase; SCS, sage 1,8-cineole synthase; SSS, sage sabinene synthase; Tris, tris(hydroxymethyl) aminomethane; UV, ultraviolet.

In accordance with the present invention, cDNAs encoding (+)-bornyl diphosphate synthase, (+)-sabinene synthase and 1,8-cineole synthase were isolated and sequenced in the following manner. An homology-based PCR strategy was utilized that is a modified version of a published, homology-based PCR strategy (Steele et al., *Proc. Natl. Acad. Sci. USA* 92:4164–4168, 1995). A comparison was made of the deduced amino acid sequences of cDNAs encoding mechanistically-related, but phylogenetically diverse, enzymes involved in terpenoid biosynthesis (Colby et al., *J. Biol. Chem.* 268:23016–23024, 1993; Yuba et al., *Arch. Biochem. Biophys.* 332:280–287, 1996; Bohlmann et al., *J. Biol. Chem.* 272:21784–21792, 1997). Three conserved regions of sequence were identified that appeared to be useful for the design of degenerate PCR primers. Two of these primers ultimately amplified a 600 bp fragment using cDNA from a phagemid sage leaf library as target. Cloning and sequencing showed that the amplified 600 bp product comprised two distinct sequence groups, both of which showed similarity to sequences of cloned terpene synthases, but only one of which hybridized strongly to a 2 kb target upon northern blot analysis of sage leaf mRNA. This more efficient probe was utilized to screen the sage leaf cDNA library, from which 77 positive phagemids were purified. Size selection of the purified and in vivo excised clones yielded a subset of 44 with inserts >1.6 kb, and these were expressed in *E. coli* XL1-Blue and assayed for functional monoterpene synthase activity by monitoring the conversion of [1-$^3$H]geranyl diphosphate to monoterpene olefins, oxygenated monoterpenes and monoterpenyl diphosphate esters.

Two cDNA clones, of which the clone designated 3C6 was more active in expression, yielded an enzyme in the corresponding bacterial extracts that produced principally bornyl diphosphate from geranyl diphosphate. This recombinant enzyme, designated SBS (sage bornyl diphosphate synthase), was presumed to represent the native (+)-bornyl diphosphate synthase of sage, one of the prominent enzymes of oil gland extracts (Croteau, R., and Karp, F., *Arch. Biochem. Biophys.* 198:512–522, 1979) that produces the first dedicated intermediate in (+)-camphor biosynthesis (Croteau, R., and Karp, F., *Arch. Biochem. Biophys.* 198:523–532, 1979; Croteau, R., and Karp, F., *Arch. Biochem. Biophys.* 184:77–86, 1977; Croteau et al., *Arch. Biochem. Biophys.* 188:182–193, 1978).

Four cDNA clones, of which clone 3B5 was apparently most active, expressed a synthase in bacterial extracts that converted geranyl diphosphate to 1,8-cineole as the major product. This acquisition was designated SCS (sage 1,8-cineole synthase) and considered to represent the native 1,8-cineole synthase, an enzyme for which the mechanism of cyclization has been studied in detail (Croteau et al., *Arch. Biochem. Biophys.* 309:184–192, 1994; Croteau, R., and Karp, F., *Arch. Biochem. Biophys.* 179:257–265, 1977).

Two additional clones, of which clone 3F25 was the more active in expression, yielded *E. coli* extracts capable of transforming geranyl diphosphate to sabinene as the dominant olefin product. This acquisition was named SSS (sage sabinene synthase), with correspondence assigned to the native (+)-sabinene synthase that catalyzes the cyclization to the bicyclic olefin precursor of (−)-isothujone (Croteau, R. in *Recent Developments in Flavor and Fragrance Chemistry* (Hopp, R., and Mori, K., eds), pp. 263–273, VCH, Weinheim, Germany, 1992; Croteau, R., in *Flavor Precursors: Thermal and Enzymatic Conversions* (Teranishi, R., Takeoka, G. R., and Guntert, M., eds), American Chemical Society Symposium Series, No. 490, pp. 8–20, Washington, DC, 1992; Karp, F., and Croteau, R., *Arch. Biochem. Biophys.* 216:616–624, 1982).

From the DNA sequence of Clones 3C6 (SEQ ID No:1), 3B5 (SEQ ID No:3) and 3F25 (SEQ ID No:5) the corresponding amino acid sequences of (+)-bornyl diphosphate synthase (SBS) (SEQ ID No:2), 1,8-cineole synthase (SCS) (SEQ ID No:4) and (+)-sabinene synthase (SSS) (SEQ ID No:6), respectively, were deduced.

Additionally, sequencing of cDNA clones that hybridized to the 600 bp prenyltransferase probe, but which did not express detectable monoterpene cyclase activity in bacterial extracts, revealed an additional clone, designated 3F5 (SEQ ID No:7). The DNA sequence of clone 3F5 is similar to the sequences of clones 3C6, 3B5 and 3F25, and appears to represent a novel monoterpene cyclase clone. Clone 3F5 contains a premature, translational stop codon, consequently clone 3F5 does not encode a functional monoterpene cyclase.

The isolation of cDNAs encoding (+)-bornyl diphosphate synthase, (+)-sabinene synthase and 1,8-cineole synthase permits the development of efficient expression systems for these functional enzymes; provides useful tools for examining the developmental regulation of monoterpene biosynthesis; permits investigation of the reaction mechanism(s) of these unusual, multiproduct enzymes, and permits the isolation of other (+)-bornyl diphosphate synthases, (+)-sabinene synthases and 1,8-cineole synthases. The isolation of the (+)-bornyl diphosphate synthase, (+)-sabinene synthase and 1,8-cineole synthase cDNAs also permits the transformation of a wide range of organisms in order to introduce monoterpene biosynthesis de novo, or to modify endogenous monoterpene biosynthesis.

Although the (+)-bornyl diphosphate synthase, 1,8-cineole synthase and (+)-sabinene synthase proteins set forth in SEQ ID Nos:2, 4 and 6, respectively, direct the enzymes to plastids, substitution of the targeting sequence of each of these enzymes (SEQ ID No:2, amino acids 1 to 56; SEQ ID No:4, amino acids 1 to 58; SEQ ID No:6, amino acids 1 to 53) with other transport sequences well known in the art (see, e.g., von Heijne et al., *Eur. J Biochem.* 180:535–545, 1989; Stryer, Biochemistry, W.H. Freeman and Company, New York, N.Y., p. 769 [1988]) may be employed to direct the (+)-bornyl diphosphate synthase, (+)-sabinene synthase and 1,8-cineole synthase to other cellular or extracellular locations.

In addition to the native (+)-bornyl diphosphate synthase, 1,8-cineole synthase and (+)-sabinene synthase amino acid sequences of SEQ ID No:2, SEQ ID No:4 and SEQ ID No:6, respectively, sequence variants produced by deletions, substitutions, mutations and/or insertions are intended to be within the scope of the invention except insofar as limited by the prior art. The (+)-bornyl diphosphate synthase, (+)-sabinene synthase and 1,8-cineole synthase amino acid sequence variants of this invention may be constructed by mutating the DNA sequences that encode the wild-type synthases, such as by using techniques commonly referred to as site-directed mutagenesis. Various polymerase chain reaction (PCR) methods, now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes in the pET (or other) overexpression vector can be employed to transform *E. coli* such as strain *E. coli* BL21(DE3)pLysS, for high level production of the mutant protein, and purification by standard protocols. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutagenesis, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that is usefully altered, although aromatics can also be substituted for alkyl side chains. Changes in the normal product distribution can indicate which step(s) of the reaction sequence have been altered by the mutation. Modification of the hydrophobic pocket can be employed to change binding conformations for substrates and result in altered regiochemistry and/or stereochemistry.

Other site directed mutagenesis techniques may also be employed with the nucleotide sequences of the invention. For example, restriction endonuclease digestion of DNA followed by ligation may be used to generate deletion variants of (+)-bornyl diphosphate synthase, (+)-sabinene synthase and 1,8-cineole synthase, as described in section 15.3 of Sambrook et al. (*Molecular Cloning: A Laboratory Manual,* 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 [1983]). Generally, oligonucleotides of at least 25 nucleotides in length are used to insert, delete or substitute two or more nucleotides in the (+)-bornyl diphosphate synthase, (+)-sabinene synthase or 1,8-cineole synthase molecule. An optimal oligonucleotide will have 12 to 15 perfectly matched nucleotides on either side of the nucleotides coding for the mutation. To mutagenize wild-type (+)-bornyl diphosphate synthase, (+)-sabinene synthase or 1,8-cineole synthase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type synthase inserted in the vector, and the second strand of DNA encodes the mutated form of the synthase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type (+)-bornyl diphosphate synthase, (+)-sabinene synthase or 1,8-cineole synthase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

A gene encoding (+)-bornyl diphosphate synthase, (+)-sabinene synthase or 1,8-cineole synthase may be incorporated into any organism (intact plant, animal, microbe, etc.), or cell culture derived therefrom, that produces geranyl diphosphate. A (+)-bornyl diphosphate synthase, (+)-sabinene synthase or 1,8-cineole synthase gene may be introduced into any organism for a variety of purposes including, but not limited to: production of (+)-bornyl diphosphate synthase, (+)-sabinene synthase or 1,8-cineole synthase, or their products; production or modification of flavor and aroma properties; improvement of defense capability, and the alteration of other ecological interactions mediated by bornyl pyrophosphate, sabinene, 1,8-cineole, or their derivatives.

Eukaryotic expression systems may be utilized for the production of (+)-bornyl diphosphate synthase, (+)-sabinene synthase and 1,8-cineole synthase since they are capable of carrying out any required posttranslational modifications and of directing the enzymes to the proper membrane location. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Bio-technology* 6:47–55 [1987]) for expression of the terpenoid synthases of the invention. Infection of insect cells (such as cells of the species *Spodoptera frugiperda*) with the recombinant baculoviruses allows for the production of large amounts of the monoterpenoid synthase proteins. In addition, the baculovirus system has other important advantages for the production of recombinant (+)-bornyl diphosphate synthase, (+)-sabinene synthase and 1,8-cineole synthase. For example, baculoviruses do not infect humans and can therefore be safely handled in large quantities. In the baculovirus system, a DNA construct is prepared including a DNA segment encoding (+)-bornyl diphosphate synthase, (+)-sabinene synthase or 1,8-cineole synthase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or “downstream” or “under the control of”) to the polyhedron gene promoter and (ii) the promoter/monoterpene synthase combination is flanked on both sides by 200–300 base pairs of baculovirus DNA (the flanking sequences).

To produce the monoterpene synthase DNA construct, a cDNA clone encoding the full length (+)-bornyl diphosphate synthase, (+)-sabinene synthase or 1,8-cineole synthase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full (+)-bornyl diphosphate synthase, (+)-sabinene synthase or 1,8-cineole synthase. For example, an insect host cell can be cotransfected or transfected separately with the DNA construct and a functional baculovirus. Resulting recombinant baculoviruses can then be isolated and used to infect cells to effect production of the monoterpene synthase. Host insect cells include, for example, *Spodoptera frugiperda* cells, that are capable of producing a baculovirus-expressed monoterpene synthase. Insect host cells infected with a recombinant baculovirus of the present invention are then cultured under conditions allowing expression of the baculovirus-encoded (+)-bornyl diphosphate synthase, (+)-sabinene synthase or 1,8-cineole synthase. (+)-Bornyl diphosphate synthase, (+)-sabinene synthase or 1,8-cineole synthase thus produced are then extracted from the cells using methods known in the art.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature* 282:39 [1979]; Kingsman et al., *Gene* 7:141 [1979]; Tschemper ct al., *Gene* 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 [1978]). Additional yeast transformation protocols are set forth in Gietz et al., *N.A.R.* 20(17):1425, 1992; Reeves et al., *FEMS* 99:193–197, 1992.

Suitable promoting sequences in yeast vectors include the promoters for 3-phosphoglycerate kinase (Hitzeman et al., *J. Biol. Chem.* 255:2073 [1980]) or other glycolytic enzymes (Hess et al., *J. Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode (+)-bornyl diphosphate synthase, (+)-sabinene synthase or 1,8-cineole synthase and a selectable marker gene, e.g., the kan gene encoding resistance to kanamycin, into *Agrobacterium tumifaciens* containing a helper Ti plasmid as described in Hoeckema et al., *Nature* 303:179–181 [1983] and culturing the Agrobacterium cells with leaf slices of the plant to be transformed as described by An et al., *Plant Physiology* 81:301–305 [1986]. Transformation of cultured plant host cells is normally accomplished through *Agrobacterium tumifaciens*, as described above. Cultures of mammalian host cells and other host cells that do not have rigid cell membrane barriers are usually transformed using the calcium phosphate method as originally described by Graham and Van der Eb (*Virology* 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffner, *Proc. Natl. Acad. Sci. USA* 77:2163 [1980]), electroporation (Neumann et al., *EMBO J.* 1:841 [1982]), and direct microinjection into nuclei (Capecchi, *Cell* 22:479 [1980]) may also be used. Additionally, animal transformation strategies are reviewed in Monastersky G. M. and Robl, J. M., Strategies in *Transgenic Animal Science*, ASM Press, Washington, D.C., 1995. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating (+)-bornyl diphosphate synthase, (+)-sabinene synthase or 1,8-cineole synthase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a (+)-bornyl diphosphate synthase, (+)-sabinene synthase or 1,8-cineole synthase gene that previously has had its native promoter removed. This engineered gene is the combination of a promoter that responds to an external chemical stimulus and a gene responsible for successful production of (+)-bornyl diphosphate synthase, (+)-sabinene synthase or 1,8-cineole synthase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993]). Representative examples include electroporation-facilitated DNA uptake by protoplasts (Rhodes et al., *Science* 240(4849):204–207 [1988]); treatment of protoplasts with polyethylene glycol (Lyznik et al., *Plant Molecular Biology* 13:151–161 [1989]); and bombardment of cells with DNA laden microprojectiles (Klein et al., *Plant Physiol.* 91:440–444 [1989] and Boynton et al., *Science* 240(4858):1534–1538 [1988]). Additionally, plant transformation strategies and techniques are reviewed in Birch, R. G., *Ann Rev Plant Phys Plant Mol Biol* 48:297 (1997); Forester et al., *Exp. Agric.* 33:15–33 (1997). Minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.* 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 [1980]); and TRI cells (Matheretal., *Annals N.Y Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of (+)-bornyl diphosphate synthase, (+)-sabinene synthase and 1,8-cineole synthase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-Kl cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enxymol.,* 204:63, 1991.

As a representative example, cDNA sequences encoding (+)-bornyl diphosphate synthase, (+)-sabinene synthase or 1,8-cineole synthase may be transferred to the $(His)_6$·Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the (+)-bornyl diphosphate synthase, (+)-sabinene synthase or 1,8-cineole synthase again purified by immobilized metal ion affinity chromatography, this time using a shallower imidazole gradient to elute the recombinant synthases while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W.H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.* 11:1657 [1983]), α-factor, alkaline phosphatase and invertase may be used to direct secretion from yeast host cells. Prokaryotic signal sequences from genes encoding, for example, LamB or OmpF (Wong et al., *Gene* 68:193 [1988]), MalE, PhoA, or beta-lactamase, as well as other genes, may be used to target proteins from prokaryotic cells into the culture medium.

As described above, the (+)-bornyl diphosphate synthase, 1,8-cineole synthase and (+)-sabinene synthase amino terminal membrane insertion sequences reside at SEQ ID No:2, amino acids 1 through 56; SEQ ID No:4, amino acids 1 through 58; SEQ ID No:6, amino acids 1 through 53) and direct the enzymes to plastids. Alternative trafficking sequences from plants, animals and microbes can be employed in the practice of the invention to direct the gene product to the cytoplasm, endoplasmic reticulum, mitochondria or other cellular components, or to target the protein for export to the medium. These considerations apply to the overexpression of (+)-bornyl diphosphate synthase, (+)-sabinene synthase and 1,8-cineole synthase, and to direction of expression within cells or intact organisms to permit gene product function in any desired location.

The construction of suitable vectors containing DNA encoding replication sequences, regulatory sequences, phenotypic selection genes and the monoterpene synthase DNA of interest are prepared using standard recombinant DNA procedures. Isolated plasmids and DNA fragments are cleaved, tailored, and ligated together in a specific order to generate the desired vectors, as is well known in the art (see, for example, Maniatis, supra, and Sambrook et al., supra).

As discussed above, (+)-bornyl diphosphate synthase, (+)-sabinene synthase and 1,8-cineole synthase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 [1982]), and Goeddel et al. (*Nucleic Acids Res.*, supra).

The following examples merely illustrate the best mode now contemplated for practicing the invention, but should not be construed to limit the invention. All literature citations herein are expressly incorporated by reference.

EXAMPLES

Example 1 cDNA Library Construction and Cloning of Monoterpene Synthases cDNA Library Preparatiom, Sage plants (*S. officinalis* L.) were grown from seed as previously described (Croteau, R., and Karp, F., *Arch. Biochem. Biophys.* 198:512–522, 1979). Approximately 15 g of emerging sage leaves (shoot tips) from three-week-old plants were ground to a fine powder in liquid nitrogen and extracted into buffer composed of 200 mM Tris-HCl (pH 8.5), 300 mM LiCl and 10 mM EDTA, and containing 1% (w/v) polyvinylpyrrolidone ($M_r$~40,000). The high concentration of chloride salts and high pH were empirically optimized to maximize the yield of intact RNA, and polyvinylpyrrolidone was found to be essential to complex co-extracted oils, resins and phenolic substances that otherwise prevent RNA isolation. Total RNA thus extracted was prepared by precipitation with isopropanol, followed by CsCl density gradient centrifugation, as previously described (Lewinsohn et al., *Plant Mol. Biol. Rep.* 12:20–25, 1994). Poly(A)$^+$ mRNA was isolated by chromatography on oligo(dT)-cellulose (Qiagen) and 6.3 μg of the resulting mRNA was used to construct a λZAPII cDNA library according to the manufacturer's instructions (Stratagene).

PCR-Based Probe Generation and Library Screening Protein purification from sage, as the basis for cDNA isolation, has been of limited success (McGeady, P., and Croteau, R., *Arch. Biochem. Biophys.* 317:149–155, 1995) because of the number of synthases present and their similarity in physical properties (Alonso, W. R., and Croteau, R., in *Methods in Plant Biochemistry* (*Enzymes of Secondary Metabolism*) (Lea, P. J., ed) Vol. 9, pp. 239–260, Academic Press, New York, 1993), and thus far has not permitted a reverse genetic approach to cloning of any of the monoterpene synthases from this species. Consequently, a generic strategy for the homology-based PCR cloning of terpenoid synthases of higher plant origin was utilized (Steele et al., *Proc. Natl. Acad. Sci. USA* 92:4164–4168, 1995), in this instance by comparing monoterpene synthase cDNA sequences that were isolated from both angiosperms and gymnosperms (Colby et al., *J. Biol. Chem.* 268:23016–23024, 1993; Yuba et al., *Arch. Biochem. Biophys.* 332:280–287, 1996; Bohlmann et al., *J. Biol. Chem.* 272:21784–21792, 1997).

Three PCR oligonucleotide primers were synthesized based on the results of the monoterpene synthase homology comparison:

1F 5'AA(G/A)AA(T/C)GA(G/A)(G/A)A(G/A)GGIGAITA (C/T)AA(G/A)GA-3' (SEQ ID No:8)

2F 5'-(T/C)TICA(G/A)(C/T)TITA(T/C)GA(G/A)GC-3' (SEQ ID No:9)

3R 5'-CT(A/G)GT(C/T)(G/A)AIGGI(C/A)T(G/A)AT(G/A) TACGT(C/T)-3' (SEQ ID No:10)

Each of the sense primers (1F and 2F) was used for PCR in combination with antisense primer (3R). Using purified sage leaf cDNA library phage as template (5 μl at $1.5\times10^9$ plaque forming units/ml), PCR was performed in a total volume of 50 μl containing 20 mM Tris-HCl (pH 8.4), 50 mM KCl, 5 mM $MgCl_2$, 200 μM of each dNTP, 5 μM of each primer and 2.5 units of Taq polymerase (BRL or Life Sciences). The thermal cycler performed the following denaturation, annealing and amplification steps: denaturation at 94° C., 1 minute; annealing at 60° C., 1 minute; extension at 72° C., 3.5 minutes; 35 cycles with final extension at 72° C., five minutes. Analysis of the PCR reaction products by agarose gel electrophoresis (Sambrook, J., Fritsch, E. F., and Maniatis, T. (1989) *Molecular Cloning: A Laboratory Manual,* 2nd Ed., pp. 2.69–2.76, Cold Spring Harbor Laboratory, Cold Spring Harbor, N.Y.) indicated that only the combination of primers 2F and 3R amplified a discrete product of approximately 600 bp, which was gel purified, ligated into pT7Blue (Novagen), and transformed into *E. coli* NovaBlue cells. Plasmid DNA was prepared from 32 individual transformants and the inserts partially sequenced (DyeDeoxy Terminator Cycle Sequencing; Applied Biosystems) to reveal that two distinct "terpenoid synthase-like" sequences had been amplified in roughly comparable amounts (SEQ ID No:11 and SEQ ID No:12).

The relative ability of these two potential probes to hybridize with expressed genes was evaluated by RNA-DNA hybridization. Two samples of sage leaf mRNA isolated as above (3 μg each) were electrophoresed on 1% (w/v) agarose under denaturing conditions and blotted onto separate PVDF membranes using standard techniques (Sambrook et al., *Molecular Cloning: A Laboratory Manual,* 2nd Ed., pp. 2.69–2.76, Cold Spring Harbor Laboratory, Cold Spring Harbor, N.Y., 1989). Each membrane was evaluated with $^{32}P$ labeled probe, generated from one or the other of the 600 bp fragments using random hexamer priming (Tabor et al., *Current Protocols in Molecular Biology* (Ausubel et al., eds), sections 3.5.9–3.5.10, John Wiley & Sons, New York, 1991), by standard hybridization and washing protocols (Sambrook et al., *Molecular Cloning: A Laboratory Manual,* 2nd Ed., pp. 2.69–2.76, Cold Spring Harbor Laboratory, Cold Spring Harbor, N.Y., 1989). Autoradiography of the membrane revealed that both probes hybridized to a 2 kb transcript, although one probe (SEQ ID No:11) generated a significantly stronger signal (~10-fold) than the other (SEQ ID No:12). The probe generating the stronger signal (SEQ ID No:11) was subsequently employed to screen the cDNA library in an attempt to isolate full-length cDNA sequences encoding the corresponding terpene synthase.

UV-crosslinked nitrocellulose lifts containing 3–$5\times10^4$ primary plaques (plated on *E. coli* XL1-Blue-MRF'), after pre-hybridization (in 1.25× SSPE, 0.5× Denhart's reagent, 9% formamide, 0.002% SDS, and 10 μg/ml denatured *E. coli* DNA, for 2 h at 42° C.), were hybridized in the same medium with approximately 8 μCi of the $^{32}P$ labeled probe for 48 h. Filters were washed, first at room temperature (in 2× SSC with 0.1% SDS), then at 55° C. (in 1× SSC with 0.1% SDS), and subsequently exposed to X-ray film at −70° C. (Sambrook et al., *Molecular Cloning: A Laboratory Manual,* 2nd Ed., pp. 2.69–2.76, Cold Spring Harbor Laboratory, Cold Spring Harbor, N.Y., 1989). Plaques yielding positive signals were purified through two additional rounds of hybridization. A total of 77 purified λZAP clones so isolated were excised in vivo to generate BluescriptII SK(−) phagmids and transformed into *E. coli* XLOLR cells according to the Stratagene protocol. The size of each cDNA insert was determined by PCR using T3 and T7 primers, and transformed clones containing an insert >1.6 kb were either expressed to assay for monoterpene synthase activity or sequenced at the 5'-terminus using the T3 promoter primer. Bluescript plasmids expressing synthase activity in cell-free extracts of transformed *E. coli* (see Examples 2 and 3) were fully sequenced on both DNA strands by primer walking or by the method of nested deletions using exonuclease III and mung bean nuclease (Sambrook et al., *Molecular Cloning. A Laboratory Manual,* 2nd Ed., pp. 2.69–2.76, Cold Spring Harbor Laboratory, Cold Spring Harbor, N.Y., 1989).

To improve functional expression and facilitate subsequent enzyme purification, each of the apparent full-length pBluescript clones that expressed monoterpene synthase activity was subcloned in frame into pGEX vectors (Pharmacia) using a convenient BamHI (SBC and SSS) or EcoRI (SCS) restriction site at the 5'-end, and the XhoI restriction site at the 3'-terminus. Fidelity in subcloning was confirmed by complete sequencing, and these plasmid constructs were expressed in *E. coli* XL1-Blue-MFR' cells.

Example 2

Expression of Monoterpene Synthase cDNAs in *E. coli*

The bluescript plasmids expressed in *E. coli* strain XL1-Blue were grown in 5 ml LB medium (Sambrook et al., *Molecular Cloning. A Laboratory Manual,* 2nd Ed., pp. 2.69–2.76, Cold Spring Harbor Laboratory, Cold Spring Harbor, N.Y., 1989), supplemented with 100 μg ampicillin/ml, to an $A_{600}$=0.5 at 37° C. with constant shaking, then induced with 1 to 3 mM IPTG. The cells were allowed an additional 4 h growth at 37° C. before harvesting by centrifugation (2000× g, 10 min) and lysis by sonication (Braun-Sonic 2000 with microprobe at maximum power for 15 seconds), on ice, in 50 mM Mopso buffer containing 10% glycerol, 10 mM $MgCl_2$ and 5 mM DTT (pH either 6.5 or 7.1, as appropriate). The sonicates were cleared by centrifugation (18,000× g, 10 min) and the resulting supernatant was used as the enzyme source. The pGEX constructs in *E. coli* XLl-Blue-MFR' cells were similarly grown at 37° C. to $A_{600}$=1.0 to 1.5, then induced with 1 mM IPTG and incubated overnight at 20° C. with constant shaking. The cells were then harvested and lysed, and the soluble supernatant prepared as before. Purification of the resulting fusion proteins was attempted using the glutathione-Sepharose affinity column according to the manufacturer's instructions (Pharmacia).

Of the three expressed monoterpene synthases (SBS, SCS and SSS), only one (SBS) bound to the matrix but, even in this case, affinity-based purification proved to be unreliable. Therefore, partial purification of the heterologously expressed synthases was achieved by ion-exchange chromatography on DEAE-cellulose (Whatman DE-52) using a 0–400 mM NaCl gradient. The partially purified preparations were desalted by repeated ultrafiltration and dilution using an Amicon Centriprep 30 concentrator (30 kDa cutoff) and the appropriate assay buffer. The pGEX-expressed fusion proteins were also subjected to gel permeation chromatography (Pharmacia FPLC system) using a Pharmacia XY 16×70 column packed with Superdex S-200 and equilibrated with the appropriate 50 mM Mopso buffer system. The column was developed at a flow rate of 0.3 ml per min and was calibrated using the Sigma MW-GF-200 molecular weight marker kit. $K_{av}$ values of the recombinant enzymes were compared to the calibration standards to establish molecular weights (Cooper, T. G. *The Tools of Biochemistry*, John Wiley & Sons, New York, 1977), which were then corrected for the engineered fusion and transit peptide to estimate the molecular weight of the corresponding native form.

Example 3

Monoterpene Synthase Assays and Product Identification

Monoterpene Synthase Assays. [1-$^3$H]Geranyl diphosphate (250 Ci/mol) was prepared by an established method (Croteau et al., *Arch. Biochem. Biophys.* 309:184–192, 1994). Terpenoid standards were from our own collection. Unless otherwise stated, all reagents were obtained from Sigma Chemical Co. or Aldrich Chemical Co.

Monoterpene synthase activities were assayed by methods previously described (Croteau, R., and Karp, F., *Arch. Biochem. Biophys.* 198:512–522, 1979; Croteau et al., *Arch. Biochem. Biophys.* 309:184–192, 1994; Gambliel, H., and Croteau, R., *J. Biol. Chem.* 259:740–748, 1984; Croteau, R., and Cane, D. E., *Methods Enzymol.* 110:383–405, 1985). Briefly, an aliquot of the bacterial cell lysate, appropriate column fractions, or partially purified and desalted enzyme preparation, in 0.5 or 1.0 ml of 50 mM Mopso buffer (pH 6.1 to 7.0, as appropriate for the target activity) containing 10 mM $MgCl_2$, 5 mM DTT and 10% (v/v) glycerol, was transferred to a 7 ml glass, Teflon sealed, screw-capped tube, and the mixture was overlayed with 1 ml pentane to trap volatile products. The reaction was initiated by the addition of 4.5 $\mu$M [1-$^3$H]geranyl diphosphate (1.3 $\mu$Ci), with incubation at 31° C. with gentle shaking for 0.5 to 3.0 h. The pentane layer and an additional pentane extract (2×1 ml) were passed over a short column of silica gel surmounted by anhydrous $MgSO_4$ (in a Pasteur pipette) to afford the monoterpene olefin fraction. Subsequent extraction of the remaining aqueous phase with diethyl ether (2×1 ml), and passage of this extract through the same column, yielded the oxygenated monoterpene fraction. The residual aqueous phase was then treated with excess potato apyrase and wheat germ acid phosphatase to hydrolyze monoterpenol diphosphate esters (Croteau, R., and Karp, F., *Arch. Biochem. Biophys.* 198:512–522, 1979; Croteau, R., and Cane, D. E., *Methods Enzymol.* 110:383–405, 1985). The liberated alcohols were then extracted into diethyl ether (2×1 ml) and the combined extract dried over anhydrous $MgSO_4$. Radioactivity in the various fractions was determined by liquid scintillation counting of aliquots (Packard 460 CD with external standard quench correction) and the remaining material was concentrated for radio-GC and GC-MS analysis.

Kinetic analyses were carried out with the partially purified, recombinant pGEX fusion proteins by determination of initial reaction rates at a minimum of ten substrate concentrations ranging from 0.45 to 45 $\mu$M [1-$^3$H]geranyl diphosphate, at saturating levels of the divalent metal ion cofactor. The results were analyzed by non-linear regression of the Michaelis-Menten equation using the curve-fitting capabilities of Sigma-Plot (Jandel Corp.).

Product Identification—To obtain sufficient product for analysis by radio-GC and chiral phase capillary GC-MS, the samples from multiple assays were pooled as necessary. Radio-GC was performed on a Gow-Mac 550P gas chromatograph with thermal conductivity detector directly coupled to a Packard 894 gas proportional counter (30). An AT-1000 packed column (Alltech) was used with He as carrier at 30 ml/min and with temperature programming from 70° C. to 200° C. (at 5° C./min) for analysis of monoterpene olefins, and from 100° C. to 200° C. (at 5° C./min) for analysis of oxygenated monoterpenes. Authentic standards (10–20 $\mu$g/component) were included with each injection in order to correlate retention times determined by mass and radioactivity detectors.

GC-MS was performed on a Hewlett-Packard 6890 GC-quadrupole mass selective detector system interfaced with a Hewlett-Packard Chemstation for data analysis. Chiral phase separations were performed by split injection (25:1) on a 30 m cyclodex-B capillary column (J&W Scientific) using He as carrier at 0.6 ml/min and temperature programming from 35° C. to 200° C. at 10° C./min.

Example 4

Product Profiles of Recombinant Synthases

Since the formation of multiple products from geranyl diphosphate is a common, if unusual, feature of the monoterpene synthases (Croteau, R., *Chem. Rev.* 87:929–954, 1987; Wise, M. L., and Croteau, R., in *Comprehensive Natural Products Chemistry: Isoprenoids* (Cane, D. E., ed) Vol. 2 (in press), Elsevier Science, Oxford, 1998), the product profiles of the recombinant enzymes were examined in detail by radio-GC and GC-MS. Recombinant sabinene synthase (SSS) produces exclusively monoterpene olefins, which by radio-GC were identified as sabinene (62%), γ-terpinene (21%), terpinolene (6.7%), limonene (6.5%) and myrcene (2.5%). The major products of this enzyme (sabinene and γ-terpinene) are formed by a cyclization mechanism involving a 1,2-hydride shift in the α-terpinyl cation intermediate. Chiral phase capillary GC-MS demonstrated the biosynthetic sabinene to be coincident with authentic (+)-sabinene; however, the (−)-enantiomer was not available for analysis to confirm the absolute configuration of this product. Previous studies have shown that cell-free extracts from sage produce only the (+)-antipode of sabinene from geranyl diphosphate (Croteau, R., in *Recent Developments in Flavor and Fragrance Chemistry* (Hopp, R., and Mori, K., eds), pp. 263–273, VCH, Weinheim, Germany, 1992; Croteau, R., in *Flavor Precursors: Thermal and Enzymatic Conversions* (Teranishi, R., Takeoka, G. R., and Guntert, M., eds), American Chemical Society Symposium Series, No. 490, pp. 8–20, Washington, DC, 1992), supporting the assignment of the (+)-stereoisomer in this case. The other principal olefinic products of SSS are achiral.

Cineole synthase (SCS) was shown by aliquot counting and radio-GC of the various metabolite fractions to produce both oxygenated monoterpenes (1,8-cineole, 79%, with a few percent α-terpineol) and a mixture of olefins (~20%). Chiral phase capillary GC-MS allowed resolution, confirmation and quantification of the olefins as (+)-α-pinene (5.5% of total products), (−)-α-pinene (0.9%), myrcene (2.9%), sabinene (2.6%, presumably the (+)-enantiomer), (+)-β-pinene (2.7%), (−)-β-pinene (4.1%), (+)-limonene (1.1%) and (−)-limonene (0.4%). The stereochemistry of the enzymatic transformation leading to 1,8-cineole has been examined (Croteau et al., *Arch. Biochem. Biophys.* 309:184–192, 1994) and shown to involve the cyclization of the bound intermediate 3R-linalyl diphosphate in anti,endo-conformation, i.e., the same overall stereochemistry required for the production of (+)-α-pinene, (+)-β-pinene and (+)-limonene (Gambliel, H., and Croteau, R., *J. Biol. Chem.* 259:740–748, 1984). The formation of the (−)-series of antipodes must therefore occur via the extended (anti,exo) conformation. This apparent loss of stereochemical fidelity in the production of some of the olefin by-products may be a consequence of the fact that the enzyme is expressed as the pGEX fusion of the preprotein of the native synthase, and thus bears a large amino-terminal extension that could compromise substrate and intermediate binding conformations.

Bornyl diphosphate synthase (SBS) was shown, by radio-GC evaluation of all metabolite fractions, to produce principally bornyl diphosphate (75%), as demonstrated by enzymatic hydrolysis of this product followed by separation of the derived borneol from the residual geraniol (liberated from the substrate) and from lesser amounts of non-enzymatic solvolysis products (also generated from geranyl diphosphate in the course of the analysis). The production of bornyl diphosphate by this recombinant enzyme was also demonstrated directly by radio-HPLC analysis of the aqueous reaction mixture using an ion-paring, reversed-phase chromatography protocol previously established for the separation of prenyl diphosphate esters (McCaskill, D., and Croteau, R., *Anal. Biochem.* 215:142–149, 1993). Additionally, chiral phase capillary GC-MS analysis of the derived borneol demonstrated the exclusive presence of the (+)-antipode, as expected based on studies with the corresponding native enzyme (Croteau, R., and Karp, F., *Arch. Biochem. Biophys.* 198:512–522, 1979; Croteau et al., *J. Biol. Chem.* 260:5956–5962, 1985; Croteau et al., *J. Biol. Chem.* 261:13438–13445, 1986).

The recombinant (+)-bornyl diphosphate synthase was also shown, by radio-GC of the olefin fraction and chiral phase GC analysis, to produce a series of olefins (25% of total product) identified as (+)-α-pinene (3.4% of total product), (+)-camphene (9.5%), (−)-camphene (0.5%), (+)-limonene (3.9%), (−)-limonene (3.9%), terpinolene (2.1%) and myrcene (1.5%). Since formation of the (+)-olefin series is mechanistically related to the formation of (+)-bornyl diphosphate via the anti,endo-cyclization of the intermediate 3R-linalyl diphosphate (Croteau et al., *J. Biol. Chem.* 264:2075–2080, 1989; Croteau et al., *J. Biol. Chem.* 260:5956–5962, 1985; Croteau et al., *J. Biol. Chem.* 261:13438–13445, 1986; Croteau et al., *J. Biol. Chem.* 263:10063–10071, 1988; Croteau et al., *Arch. Biochem. Biophys.* 277:374–381, 1990), the generation of small amounts of the antipodal (−)-camphene and (−)-limonene by the recombinant cyclase again suggests some loss of stereochemical fidelity in the overall reaction sequence.

Example 5

Sequence Analysis of Recombinant Synthases

DNA sequences were assembled and analyzed using GCG software (Wisconsin Package version 9.0, Genetics Computer Group (GCG), Madison, Wis.). Alignment of the deduced amino acid sequences of SBS clone 3C6 (SEQ ID No:1) (2025 bps, with an ORF of 1794 nts encoding 598 amino acids for a protein of 69.3 kDa and calculated pI of 6.06), SCS clone 3B5 (SEQ ID No:3) (1968 bps, with an ORF of 1773 nts encoding 591 amino acids for a protein of 69.4 kDa and calculated pI of 5.79), and SSS clone 3F25 (SEQ ID No:5) (1911 bps, with an ORF of 1767 nts encoding 589 amino acids for a protein of 68.9 kDa and calculated pI of 5.22), with the published sequences for (−)-limonene synthase from *Mentha spicata* (spearmint) (Colby et al., *J. Biol. Chem.* 268:23016–23024, 1993) and *Perilla frutescens* (Yuba et al., *Arch. Biochem. Biophys.* 332:280–287, 1996), linalool synthase from *Clarkia breweri* (Dudareva et al., *Plant Cell* 8:1137–1148, 1996), and three monoterpene olefin synthases from Abies grandis (grand fir) (Bohlmann et al., *J. Biol. Chem.* 272:21784–21792, 1997), illustrates that there are several regions of similarity between these nine monoterpene synthases of diverse origin. Comparison of these sequences using the GCG GAP program (Wisconsin Package version 9.0, Genetics Computer Group (GCG), Madison, Wis.) revealed the monoterpene synthases from sage to resemble each other and the limonene synthases from related members of the Lamiaceae (50–70% identity, 70–85% similarity) more closely than the monoterpene synthases of the gymnosperm grand fir (−32% identity) or the linalool synthase from *C. breweri* (−25% identity).

Monoterpene biosynthesis is compartmentalized in plastids (Gleizes et al., *Planta* 159:373–381, 1983; Mettal et al., *Eur. J. Biochem.* 170:613–616, 1988; Perez et al., *Plant Physiol. Biochem.* 28:221–229, 1990), thus the monoterpene synthases are encoded as preproteins bearing an amino-terminal transit peptide for import of these nuclear gene products into plastids (leucoplasts of the oil gland cells in the present instance) where they are proteolytically processed to the mature forms (Keegstra et al., *Annu. Rev. Plant Physiol. Plant Mol. Biol.* 40:471–501, 1989). In all of the monoterpene synthases thus far examined, the 50 to 60 amino terminal residues are characterized by a low degree of similarity, typical of targeting sequences, yet they all share common features of transit peptides in being rich in serine, threonine and small hydrophobic residues but with few acidic residues (Keegstra et al., *Annu. Rev. Plant Physiol. Plant Mol. Biol.* 40:471–501, 1989; von Heijne et al., *Eur. J. Biochem.* 180:535–545, 1989).

All native monoterpene synthases thus far examined appear to be N-terminally blocked, preventing direct determination (by sequencing) of the transit peptide-mature protein cleavage junction (Lewinsohn et al., *Arch. Biochem. Biophys.* 293:167–173, 1992; McGeady, P., and Croteau, R., *Arch. Biochem. Biophys.* 317:149–155, 1995; Steele et al., *Proc. Natl. Acad. Sci. USA* 92:4164–4168, 1995; Colby et al., *J. Biol. Chem.* 268:23016–23024, 1993). Significantly, a tandem pair of arginine residues (e.g., $arg^{55}$ $arg^{56}$ of SBS, $arg^{57}$ $arg^{58}$ of SCS and $arg^{52}$ $arg^{53}$ of SSS) are strictly conserved in the deduced sequences of all of the monoterpene synthases and they define the most N-terminal region of obvious homology, suggesting a possible cleavage site. It is believed that truncation of the recombinant (+)-bornyl diphosphate synthase, 1,8-cineole synthase and (+)-sabinene synthase preproteins immediately upstream of these tandem arginines will yield fully functional "pseudomature" forms of the enzymes, whereas truncation downstream from this element will severely impair activity.

Downstream of the aforementioned, tandem arginines are several regions of homology, including the universally conserved (I,L or V)DDXXD (SEQ ID No:13) motif (e.g., residues $I^{350}$-$D^{355}$ of SBS) (SEQ ID No:2) found in virtually all deduced sequences for enzymes that utilize prenyl diphosphate substrates (Chen et al., *Protein Sci.* 3:600–607, 1994; Chen et al., *Arch. Biochem. Biophys.* 324:255–266, 1995). This aspartate rich element is now generally recognized as a binding site for the metal ion chelated diphosphate ester substrate (Chen et al., *Protein Sci.* 3:600–607, 1994; Ashby, M. N., and Edwards, P. A., *J. Biol. Chem.* 265:13157–13164, 1990; Tarshis et al., *Biochemistry* 33:10871–10877, 1994; Cane et al., *Biochemistry* 33:5846–5857, 1994; Tarshis et al., *Proc. Natl. Acad. Sci. USA* 93:15018–15023, 1996). Several other highly conserved regions are also apparent including, with reference to the amino acid sequence of SBS (SEQ ID No:2): $Arg^{298}$-Trp-$Trp^{300}$, $Arg^{372}$-Trp-Glu/$Gln^{374}$, $Tyr^{384}$-Met-Gln/$Lys^{386}$ and $Cys^{516}$-Tyr-Met-X-Glu/$Asp^{520}$ (SEQ ID No:14). The active site peptide LQLYEASFLL (SEQ ID No:15), previously isolated from the co-purified (+)-pinene synthase and (+)-bornyl diphosphate synthase of sage (McGeady, P., and Croteau, R., *Arch. Biochem. Biophys.* 317:149–155, 1995) was located at residues 195–204 of SBS (SEQ ID No:2) and also at residues 187–196 of SSS (SEQ ID No:6). Very similar sequences in the same location were found in SCS (SEQ ID No:4, amino acid residues 191–200) and in the two limonene synthase sequences from *M. spicata* and *P. frutescens.*

The (+)-bornyl diphosphate synthase from sage has previously been shown to be inhibited by the 'active serine'-directed reagent diisopropylfluorophosphate (Croteau, R., and Karp, F., *Arch. Biochem. Biophys.* 198:512–522, 1979), a characteristic not shared by other monoterpene cyclases (Alonso, W. R., and Croteau, R., in *Methods in Plant Biochemistry* (*Enzymes of Secondary Metabolism*) (Lea, P. J., ed) Vol. 9, pp. 239–260, Academic Press, New York, 1993). Because of the unique utilization of the substrate diphosphate moiety as the terminating nucleophile by this enzyme (Cane et al., *J. Am. Chem. Soc.* 104:5831–5833, 1982; Croteau et al., *Biochemistry* 24:7077–7085, 1985), it was hypothesized that a serine residue may be involved in binding and transfer of the diphosphate function in the course of the reaction. Sequence comparison of SBS with the other two monoterpene synthases of sage reveals four unique serine residues at positions 302, 320, 454 and 469 (SEQ ID No:2). Two (at positions 302 and 320) are within otherwise highly conserved regions and are, therefore, obvious targets for selective covalent modification with radiolabeled diisopropylfluorophosphate and directed mutagenesis studies.

Example 6

Physical Properties of Recombinant Synthases

Properties of SBS Calibrated gel permeation chromatography of the pGEX fusion form of SBS revealed a single peak of activity at an elution volume corresponding to an $M_r$~200,000, indicating that the expressed fusion preprotein (corresponding to a molecular weight of about 2x96,300) was a functional dimer. Treatment of the SBS protein with thrombin to remove the glutathione-S-transferase fusion tag, followed by re-chromatography, indicated a decrease in molecular weight to approximately 135,000, consistent with the loss of the 27 kDa transferase peptide from each subunit at a calculated molecular weight of 69,300 for the preprotein. Further correction of the molecular weight to account for the transit peptide would yield a dimer of about 120 kDa which corresponds roughly to the native dimer molecular weight of both (+)-bornyl diphosphate synthase and (+)-pinene synthase from sage (Croteau, R., and Karp, F., *Arch. Biochem. Biophys.* 198:512–522, 1979 Gambliel, H., and Croteau, R., *J. Biol. Chem.* 259:740–748, 1984), two enzymes which have never been satisfactorily resolved as distinct species. Although a dimeric quartemary structure is not unique to these two synthases, the vast majority of the monoterpene synthases characterized to date are monomeric (Alonso, W. R., and Croteau, R., in *Methods in Plant Biochemistry* (*Enzymes of Secondary Metabolism*) (Lea, P. J., ed) Vol. 9, pp. 239–260, Academic Press, New York, 1993).

The product profile of the protein encoded by SBS clone 3C6 (SEQ ID No:2) is qualitatively similar to the combination of both (+)-bornyl diphosphate synthase and (+)-pinene synthase (i.e., (+)-bornyl diphosphate and the (+)-series of α-pinene and related olefins) (Croteau, R., and Karp, F., *Arch. Biochem. Biophys.* 198:512–522, 1979; Gambliel, H., and Croteau, R., *J. Biol. Chem.* 259:740–748, 1984), although the quantitative distributions do not exactly match, and the stereochemistry of the olefin products is anomalous. Thus, (+)-bornyl diphosphate and (+)-α-pinene, (+)-camphene and (+)-limonene arise via the same overall cyclization stereochemistry, and these enantiomers are produced exclusively from geranyl diphosphate by the native (+)-bornyl diphosphate and (+)-pinene synthase activities (Croteau et al., *J. Biol. Chem.* 264:2075–2080, 1989; Croteau et al., *J. Biol Chem.* 260:5956–5962, 1985; Croteau et al., *J. Biol. Chem.* 261:13438–13445, 1986; Croteau et al., *J. Biol. Chem.* 263:10063–10071, 1988; Croteau et al., *Arch. Biochem. Biophys.* 277:374–381, 1990).

The small amounts of (−)-limonene and (−)-camphene formed by the recombinant enzyme are attributed to antipodal cyclizations via abnormal extended conformations, as the phenomenon has been described previously, especially when using neryl diphosphate (the cis-analog of geranyl diphosphate) as an alternate substrate (Croteau et al., *J. Biol. Chem.* 263:10063–10071, 1988; Croteau, R., and Satterwhite, D. M., *J. Biol. Chem.* 264:15309–15315, 1989). The geranyl substrate, however, was verified as >99% pure, thereby eliminating this possibility in the present instance and suggesting that loss of stereochemical fidelity (to the extent of 5% of the total product mixture) may be attributed to the presence of the glutathione-S-transferase fusion peptide plus transit peptide which may alter substrate binding directly, or indirectly by compromising subunit assembly.

Thus, the physical properties of the recombinant (+)-bornyl diphosphate synthase, together with the distribution and stereochemistry of its products, suggest that this enzyme might represent both (+)-bornyl diphosphate synthase and (+)-pinene synthase which were previously assumed to be distinct enzymes. The resolution of this question will require the detailed assessment of truncated enzymes that more closely resemble the native form, and which will therefore be likely to produce the same mixture of monoterpenes as the native form.

Physical Properties of SCS and SSS. Gel permeation chromatography of SCS revealed a single peak of activity at an elution volume corresponding to an $M_r$ of 72,000, whereas SSS gave two peaks of activity, an aggregated form eluting in the void volume and a second corresponding to an $M_r$ of 60,000. Both of these molecular weights are significantly lower than those predicted from pGEX expression-based fusion of the glutathione-S-transferase (27 kDa) with the respective preproteins (SCS ~96 kDa and SSS ~96 kDa). Thrombin treatment was without influence on the gel permeation chromatographic behavior of these enzymes, indicating the absence of the glutathione-S-tranferase peptide tag and rationalizing the previously observed inability of the recombinant SCS and SSS enzymes to bind to the glutathione affinity column. Inspection of the 5'-sequences of the corresponding pGEX constructs showed both to be free of in-frame stop codons that might have permitted polycistronic translation of the preprotein devoid of the glutathione-S-transferase peptide. The apparent truncation was therefore attributed to proteolytic processing of the recombinant SCS and SSS in the *E. coli* host to proteins that seemingly resemble the preprotein forms of the native, monomeric, sage 1,8-cineole synthase (Croteau et al., *Arch. Biochem. Biophys.* 309:184–192, 1994; Croteau, R., and Karp, F., *Arch. Biochem. Biophys.* 179:257–265, 1977) and (+)-sabinene synthase (Croteau, R., in *Recent Developments in Flavor and Fragrance Chemistry* (Hopp, R., and Mori, K., eds), pp. 263–273, VCH, Weinheim, Germany, 1992; Croteau, R., in *Flavor Precursors. Thermal and Enzymatic Conversions* (Teranishi, R., Takeoka, G. R., and Guntert, M., eds), American Chemical Society Symposium Series, No. 490, pp. 8–20, Washington, DC, 1992). Similar proteolytic processing of a recombinant limonene synthase preprotein from spearmint has been observed previously in this *E. coli* host (Colby et al., *J. Biol. Chem.* 268:23016–23024, 1993).

1,8-Cineole synthase has never been satisfactorily separated from the aforementioned (−)-pinene synthase from sage but, in this instance, the product distribution of SCS does not match well the product distribution of (−)-pinene synthase either quantitatively, qualitatively, or in stereochemical terms, since the reactions catalyzed are of the opposite antipodal series (Croteau et al., *Arch. Biochem. Biophys.* 309:184–192, 1994; Gambliel, H., and Croteau, R., *J. Biol. Chem.* 257:2335–2342, 1982; Croteau et al., *J. Biol. Chem.* 264:2075–2080, 1989). However, the product distribution of SCS shows some parallels with that of the recently described cyclase III which produces (+)-α-pinene and (+)-β-pinene (Wagschal et al., *Arch. Biochem. Biophys.* 308:477–487, 1994; Pyun et al., *Arch. Biochem. Biophys.* 308:488–496, 1994). Even here, the match is not perfect and the production of anomalous products of the antipodal (−)-series (<6% of total) again suggests that substrate binding interactions may be compromised by the presence of the substantial transit peptide.

To assess the latter possibility, the $K_m$ values for SCS (7.0 μM), SSS (7.4 μM) and SBS (3.0 μM) were determined. These values are likely somewhat high because the recombinant enzymes were not purified sufficiently to remove all contaminating phosphatases that result in some depletion of the substrate geranyl diphosphate. While the calculated $K_m$ values compare reasonably well with the literature values of 1.1 μM (Croteau et al., *Arch. Biochem. Biophys.* 309:184–192, 1994), 2.0 μM (Croteau, R., in *Recent Developments in Flavor and Fragrance Chemistry* (Hopp, R., and Mori, K., eds), pp. 263–273, VCH, Weinheim, Germany, 1992) and 2.0 μM (Croteau et al., *J. Biol. Chem.* 264:2075–2080, 1989; Croteau et al., *Arch. Biochem. Biophys.* 277:374–381, 1990), respectively, for the corresponding native enzymes, they are sufficiently higher to suggest at least subtle alteration in binding capacity of the recombinant forms.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleotide sequence encoding (+)-bornyl diphosphate synthase or (+)-sabinene synthase from sage.

2. A nucleotide sequence of claim 1 encoding (+)-bornyl diphosphate synthase.

3. A nucleotide sequence of claim 1 encoding (+)-bornyl diphosphate synthase from *Salvia officinalis*.

4. A nucleotide sequence of claim 1 encoding (+)-sabinene synthase.

5. A nucleotide sequence of claim 1 encoding (+)-sabinene synthase from *Salvia officinalis*.

6. An isolated nucleotide sequence encoding a protein having the enzymatic activity of SEQ ID No:2 or SEQ ID No:6.

7. An isolated nucleotide sequence of claim 6 which encodes the amino acid sequence of SEQ ID No:2, SEQ ID No:4 or SEQ ID No:6.

8. An isolated nucleotide sequence of claim 6 which encodes the amino acid sequence of SEQ ID No:2.

9. An isolated nucleotide sequence of claim 6 which encodes the amino acid sequence of SEQ ID No:4.

10. An isolated nucleotide sequence of claim 6 which encodes the amino acid sequence of SEQ ID No:6.

11. An isolated nucleotide sequence of claim 6 having the sequence of SEQ ID No:1.

12. An isolated nucleotide sequence of claim 7 having the sequence of SEQ ID No:3.

13. An isolated nucleotide sequence of claim 6 having the sequence of SEQ ID No:5.

14. A replicable expression vector comprising a nucleotide sequence encoding a protein having the enzymatic activity of SEQ ID No:2 or SEQ ID No:6.

15. A replicable expression vector wherein the nucleotide sequence comprises the sequence of SEQ ID No:1, SEQ ID No:3 or SEQ ID No:5.

16. A host cell comprising a vector of claim 14.

17. A host cell comprising a vector of claim 15.

18. A method of enhancing the expression of (+)-bornyl diphosphate synthase in a suitable host cell comprising introducing into the host cell an expression vector that comprises a nucleotide sequence encoding a protein having the enzymatic activity of SEQ ID No:2 under conditions enabling expression of the protein in the host cell.

19. A method of enhancing the expression of 1,8-cineole synthase in a suitable host cell comprising introducing into the host cell an expression vector that comprises the nucleotide sequence set forth in SEQ ID No:3 encoding a protein having the enzymatic activity of SEQ ID No:4 under conditions enabling expression of the protein in the host cell.

20. A method of enhancing the expression of (+)-sabinene synthase in a suitable host cell comprising introducing into the host cell an expression vector that comprises a nucleotide sequence encoding a protein having the enzymatic activity of SEQ ID No:6 under conditions enabling expression of the protein in the host cell.

* * * * *

UNITED STATES PATENT AND TRADEMARK OFFICE

CERTIFICATE OF CORRECTION

PATENT NO. : 5,891,697

DATED : April 6, 1999

INVENTOR(S) : R.B. Croteau et al.

It is certified that error appears in the above-identified patent and that said Letters Patent is hereby corrected as shown below:

| COLUMN | LINE | |
|---|---|---|
| [56] Pg. 1, col. 1 | Refs. Cited (Other Refs., Item 4) | "(-)-α-Pinee" should read --(-)-α-Pinene-- |
| [56] Pg. 1, col. 1 | Refs. Cited (Other Refs., Item 6) | "Monot-<br>erpene" should break as follows:<br>--Mono-<br>terpene-- |
| [56] Pg. 1, col. 2 | Refs. Cited (Other Refs., Item 11) | "Monot-<br>erpene" should break as follows:<br>--Mono-<br>terpene-- |
| [56] Pg. 1, col. 2 | Refs. Cited (Other Refs., Item 11) | "*officinalis*), " *Arch.*" should read --*officinalis*)," *Arch.*-- |
| 1 | 25 | "et at.," should read --et al.,-- |
| 1 | 26 | delete "i" |
| 3 | 44 | "1,8cineole" should read --1,8-cineole-- |
| 4 | 45 | before "1992)." insert a space |

UNITED STATES PATENT AND TRADEMARK OFFICE

CERTIFICATE OF CORRECTION

PATENT NO. : 5,891,697

DATED : April 6, 1999

INVENTOR(S) : R.B. Croteau et al.

It is certified that error appears in the above-identified patent and that said Letters Patent is hereby corrected as shown below:

| COLUMN | LINE | |
|---|---|---|
| 5 | 34 | "(+)-bomyl" should read --(+)-bornyl-- |
| 6 | 17 | "synthasc," should read --synthase,-- |
| 12 | 23 | "ct al.," should read --et al.,-- |
| 18 | 43-44 | "($M_r$~40,<br>000)." should not break |
| 20 | 26 | "*Cloning.*" should read --*Cloning*:-- |
| 20 | 45 | "*Cloning.*" should read --*Cloning*:-- |
| 21 | 50-51 | "Monot-<br>erpene" should break as follows:<br>--Mono-<br>terpene-- |
| 24 | 22-23 | "Monot-<br>erpene" should break as follows:<br>--Mono-<br>terpene-- |
| 25 | 67 | after 1979" insert --;-- |
| 26 | 3 | "quartemary" should read --quarternary-- |

UNITED STATES PATENT AND TRADEMARK OFFICE

CERTIFICATE OF CORRECTION

PATENT NO. : 5,891,697

DATED : April 6, 1999

INVENTOR(S) : R.B. Croteau et al.

It is certified that error appears in the above-identified patent and that said Letters Patent is hereby corrected as shown below:

| COLUMN | LINE | |
|---|---|---|
| 59 (Claim 7, | 28 line 1) | delete "of claim 6" |
| 59 (Claim 9, | 33 line 1) | "claim 6" should read --claim 7-- |

Signed and Sealed this

Sixth Day of June, 2000

Attest:

Q. TODD DICKINSON

*Attesting Officer*

*Director of Patents and Trademarks*